(12) United States Patent
Alperin

(10) Patent No.: US 12,124,966 B1
(45) Date of Patent: Oct. 22, 2024

(54) APPARATUS AND METHOD FOR GENERATING A TEXT OUTPUT

(71) Applicant: SurvivorNet, Inc., New York, NY (US)

(72) Inventor: Steven David Alperin, New York, NY (US)

(73) Assignee: SurvivorNet, Inc., New York, NY (US)

( * ) Notice: Subject to any disclaimer, the term of this patent is extended or adjusted under 35 U.S.C. 154(b) by 0 days.

(21) Appl. No.: 18/426,617

(22) Filed: Jan. 30, 2024

(51) Int. Cl.
*G06N 5/02* (2023.01)
*G06F 16/33* (2019.01)
*G06F 40/279* (2020.01)
*G06F 40/30* (2020.01)
*G16H 15/00* (2018.01)

(52) U.S. Cl.
CPC .......... *G06N 5/02* (2013.01); *G06F 16/3344* (2019.01); *G06F 40/279* (2020.01); *G06F 40/30* (2020.01); *G16H 15/00* (2018.01)

(58) Field of Classification Search
CPC ..... G06N 5/02; G06F 16/3344; G06F 40/279; G06F 40/30; G16H 15/00
See application file for complete search history.

(56) References Cited

U.S. PATENT DOCUMENTS

| | | | |
|---|---|---|---|
| 9,031,845 B2* | 5/2015 | Kennewick | G06F 16/3329 704/270.1 |
| 11,775,511 B2 | 10/2023 | Wang et al. | |
| 2006/0047635 A1* | 3/2006 | Kraenzel | G06F 16/9535 |
| 2021/0034705 A1* | 2/2021 | Chhaya | G06F 40/205 |
| 2021/0103606 A1* | 4/2021 | Malhotra | G06F 16/9535 |
| 2021/0397793 A1* | 12/2021 | Li | G06F 40/166 |
| 2022/0139245 A1 | 5/2022 | Wilson et al. | |
| 2022/0300716 A1* | 9/2022 | Sabharwal | G06F 16/24578 |
| 2023/0259713 A1* | 8/2023 | Religa | G06F 40/253 704/9 |

* cited by examiner

*Primary Examiner* — Eric Yen
(74) *Attorney, Agent, or Firm* — Caldwell Intellectual Property Law

(57) ABSTRACT

An apparatus for generating a text report is disclosed. The apparatus includes at least a processor and a memory communicatively connected to the at least a processor. The memory instructs the processor to receive contextual data from a user. The memory instructs the processor to generate a query as a function of the contextual data. The memory instructs the processor to receive a query response from the user as a function of the query. The memory instructs the processor to generate a return as a function of the query response using a tonal adjustment engine. The memory instructs the processor to display the response using a display device.

20 Claims, 9 Drawing Sheets

APPARATUS AND METHOD FOR GENERATING A TEXT OUTPUT

FIELD OF THE INVENTION

The present invention generally relates to the field of artificial intelligence. In particular, the present invention is directed to an apparatus and a method for generating text reports.

BACKGROUND

Chatbots experience constraints on the quality of conversations they can achieve using generic responses and prompts. Efforts to enhance their personability and response structures have proven to be a long-term issue. In fields where more nuanced communication is necessary, the medical field generic responses often lead to patient confusion and frustration.

SUMMARY OF THE DISCLOSURE

In an aspect an apparatus for generating a text report is disclosed. The apparatus includes at least a processor and a memory communicatively connected to the at least a processor. The memory instructs the processor to receive contextual data. The processor generates a query as a function of the contextual data and receives a query response as a function of the query. The processor then generates a return as a function of the query response; and a tonal adjustment engine, where the tonal adjustment engine includes training a tonal adjustment machine learning model using tonal adjustment training data, where the tonal adjustment training data includes inputs correlated to outputs. Additionally, the processor updates the tonal adjustment engine as a function of the outputs. The memory then instructs the process to display the return using a display device.

In another aspect a method for generating a text report is disclosed. The method includes receiving contextual data. The method includes generating a query as a function of the contextual data and receiving a query response as a function of the query. Then generating a return as a function of the query response and a tonal adjustment engine, where the tonal adjustment engine includes training a tonal adjustment machine learning model using tonal adjustment training data, where the tonal adjustment training data includes inputs correlated to outputs. Additionally, the method includes updating the tonal adjustment engine as a function of the outputs. The memory then instructs the process to display the return using a display device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a text report. The apparatus includes at least a processor and a memory communicatively connected to the at least a processor. The memory instructs the processor to receive a user profile. The processor generates an query as a function of the user profile and receives an query response as a function of the query. The processor then generates a response as a function of the query response using a tonal adjustment engine, where the tonal adjustment engine comprises training a tonal adjustment large language machine learning model using tonal adjustment training data, where the tonal adjustment training data comprises inputs correlated to outputs. Additionally, the processor updates the tonal adjustment engine as a function of the outputs. The memory then instructs the process to display the response using a display device.

Aspects of the present disclosure can be used to generate more user-friendly responses. Aspects of the present disclosure can also be used to generate more accurate responses. This is so, at least in part, because a tonal adjustment machine is used to at least rephrase a response to match the user profile's needs. Exemplary embodiments illustrating aspects of the present disclosure are described below in the context of several specific examples.

Figure 1:
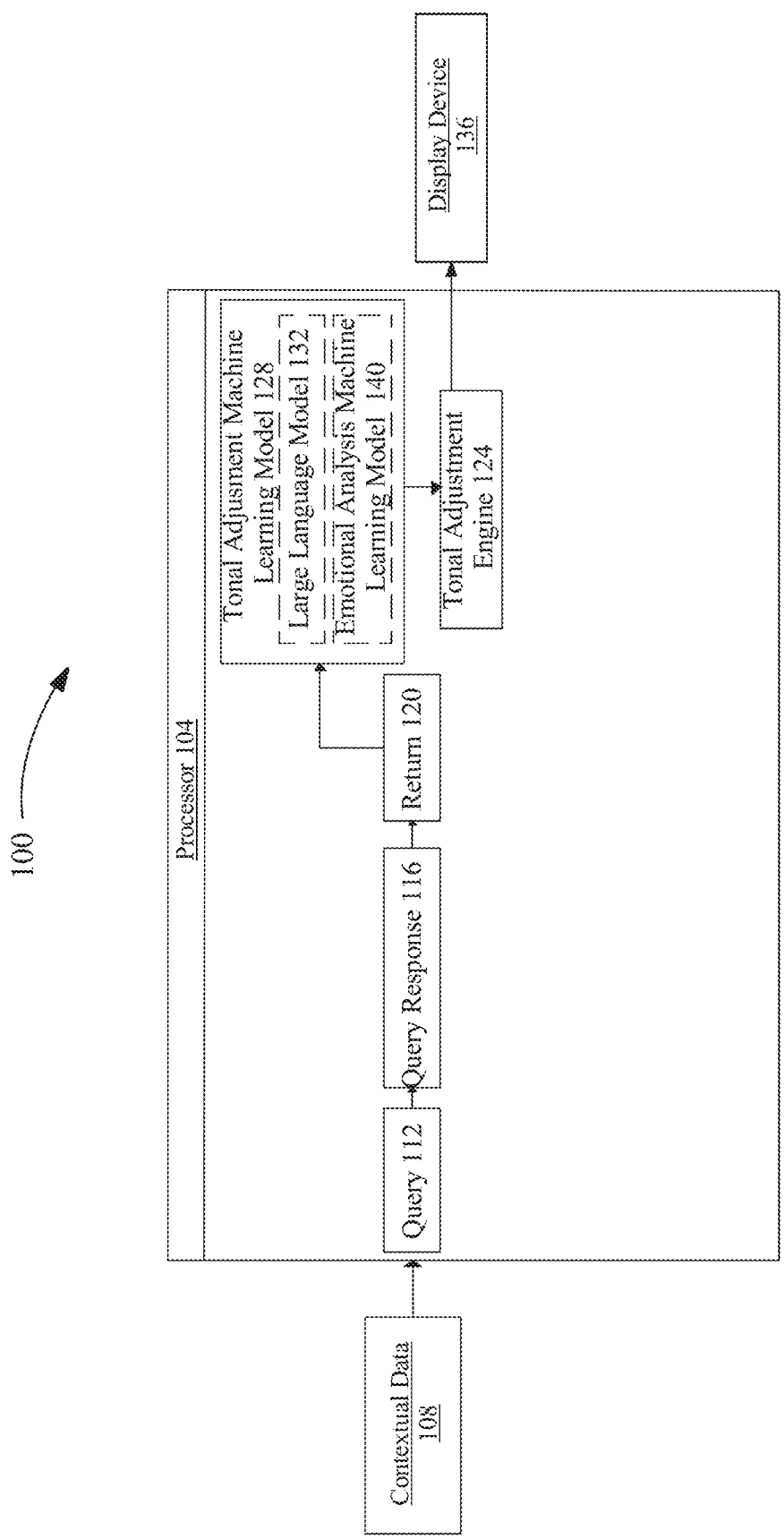
FIG. 1 is a block diagram of an exemplary embodiment of an apparatus for generating a text report.

Referring now to FIG. 1, an exemplary embodiment of apparatus 100 for generating a text report is illustrated. Apparatus 100 includes a Processor 104. Processor 104 includes a processor communicatively connected to a memory. As used in this disclosure, "communicatively connected" means connected by way of a connection, attachment, or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Further referring to FIG. 1 Processor 104 may include any computing device as described in this disclosure, including without limitation a microcontroller, microprocessor, digital signal processor (DSP) and/or system on a chip (SoC) as described in this disclosure. Processor 104 may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting Processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 Processor 104 may include but is not limited to, for example, a computing device or cluster of computing devices in a first location and a second computing device or cluster of computing devices in a second location. Processor 104 Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented, as a non-limiting example, using a "shared nothing" architecture.

With continued reference to FIG. 1, Processor 104 may be designed and/or configured to perform any method, method step, or sequence of method steps in any embodiment described in this disclosure, in any order and with any degree of repetition. For instance, Processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

With continued reference to FIG. 1, Processor 104 May be configured to receive contextual data 108. For the purposes of this disclosure, a "contextual data" is a representation of information and/or data associated with a user. Contextual data 108 May be made up of a plurality of user data. As used in the current disclosure, "user data" is information associated with a user. Contextual data 108 May be created by a Processor 104, a user, medical professional, or a third party. The contextual data 108 May include any of the following personal information: age, weight, height, gender, geographical location, insurance information, employment history, educational history, familial medical history, and the like. Contextual data 108 May be continuously updated when new information about the user is available. Continuous updating may be performed by Processor 104.

With continued reference to FIG. 1, contextual data 108 may be received by processor 104 via user input. For example, and without limitation, the user or a third party may manually input contextual data 108 using a user interface 304 or 308, as described with reference to FIG. 3, or a remote device, such as for example, a smartphone or laptop. The user profile 108 may additionally be generated using answers to a series of questions. The series of questions may be implemented using a chatbot, as described herein below. A chatbot may be configured to generate questions regarding any element of user profile 108. In a non-limiting embodiment, a user may be prompted to input specific information or may fill out a questionnaire. In another embodiment, a user may be prompted to input specific information using drop down menus, check boxes, and the like. In an additional embodiment, a graphical user interface may display a series of questions to prompt a user for information pertaining to contextual data 108. Contextual data 108 may be transmitted to processor 104, such as using a wired or wireless communication, as previously discussed in this disclosure. Contextual data 108 can be retrieved from multiple sources third-party sources including the user's inventory records, financial records, human resource records, past contextual data 108, sales records, user notes and observations, and the like. Contextual data may be placed through an encryption process for security purposes.

With continued reference to FIG. 1, processor 104 may receive contextual data 108 from a user database. In an embodiment, any past or present versions of any data disclosed herein may be stored within the user database including but not limited to the contextual data 108, biological data, user records, and the like. Processor 104 may be communicatively connected with the user database. For example, in some cases, database may be local to processor 104. Alternatively or additionally, in some cases, database may be remote to processor 104 and communicative with processor 104 by way of one or more networks. Network may include, but not limited to, a cloud network, a mesh network, or the like. By way of example, a "cloud-based" system, as that term is used herein, can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connects directly, dynamically, and non-hierarchically to as many other computing devices as possible. A "network topology" as used in this disclosure is an arrangement of elements of a communication network, user database may be implemented, without limitation, as a relational database, a key-value retrieval database such as a NOSQL database, or any other format or structure for use as a database that a person skilled in the art would recognize as suitable upon review of the entirety of this disclosure, user database may alternatively or additionally be implemented using a distributed data storage protocol and/or data structure, such as a distributed hash table or the like, user database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 1, contextual data 108 may include user records. As used in the current disclosure, a "user record" is a document that contains information regarding the user. User records may include medical records, medical history, medical tests, user credentials, doctors' notes, previous user reports, medical imaging documents, insurance information, and government records (i.e., birth certificates, social security cards, and the like). User records may be identified using a web crawler. User records may include a variety of types of "notes" entered over time by the user, medical providers, third-parties, medical professionals, and the like. User records may be converted into machine-encoded text using an optical character reader (OCR).

Still referring to FIG. 1, in some embodiments, optical character recognition or optical character reader (OCR) includes automatic conversion of images of written (e.g., typed, handwritten, or printed text) into machine-encoded text. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 1, in some cases, OCR may be an "offline" process, which analyses a static document or image frame. In some cases, handwriting movement analysis can be used as input for handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image components. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to the image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from the background of the image component. In some cases, binarization may be required for example if an employed OCR algorithm only works on binary images. In some cases, a line removal process may include the removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify a script allowing an appropriate OCR algorithm to be selected. In some cases, a character isolation or "segmentation" process may separate signal characters, for example, character-based OCR algorithms. In some cases, a normalization process may normalize the aspect ratio and/or scale of the image component.

Still referring to FIG. 1, in some embodiments, an OCR process will include an OCR algorithm. Exemplary OCR algorithms include matrix-matching process and/or feature extraction processes. Matrix matching may involve comparing an image to a stored glyph on a pixel-by-pixel basis. In some cases, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at the same scale as input glyph. Matrix matching may work best with typewritten text.

Still referring to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted features can be compared with an abstract vector-like representation of a character, which might reduce to one or more glyph prototypes. General techniques of feature detection in computer vision are applicable to this type of OCR. In some embodiments, machine-learning processes like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIGS. 5-7. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1, in some cases, OCR may employ a two-pass approach to character recognition. The second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool includes OCRopus. OCRopus development is led by German Research Centre for Artificial Intelligence in Kaiserslautern, Germany. In some cases, OCR software may employ neural networks, for example neural networks as taught in reference to FIGS. 2, 4, and 5.

Still referring to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make use of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

With continued reference to FIG. 1, contextual data 108 may be generated using a web crawler. A "web crawler," as used herein, is a program that systematically browses the internet for the purpose of Web indexing. The web crawler may be seeded with platform URLs, wherein the crawler may then visit the next related URL, retrieve the content, index the content, and/or measures the relevance of the content to the topic of interest. In some embodiments, processor 104 may generate a web crawler to compile the contextual data 108 and biological data. The web crawler may be seeded and/or trained with a reputable website, such as the user's medical provider's website, to begin the search. A web crawler may be generated by a processor 104. In some embodiments, the web crawler may be trained with information received from a user through a user interface. In some embodiments, the web crawler may be configured to generate a web query. A web query may include search criteria received from a user. For example, a user may submit a plurality of websites for the web crawler to search to extract user records, past contextual data 108, notes, and observations, based on criteria such as a time, location, and the like.

With continued reference to FIG. 1, processor 104 may be configured to receive contextual data 108 using an application programming interface (API). As used herein, an "application programming interface" is a set of functions that allow applications to access data and interact with external software components, operating systems, or microdevices, such as another web application or computing device. An API may define the methods and data formats that applications can use to request and exchange information. APIs enable seamless integration and functionality between different systems, applications, or platforms. An API may deliver contextual data 108 to apparatus 100 from a system/application that is associated with a user or other third-party custodian of user information. An API may be configured to query for web applications or other websites to retrieve contextual data 108 or other data associated with the user. An API may be further configured to filter through web applications according to a filter criterion. In this disclosure, "filter criterion" are conditions the web applications must fulfill in order to qualify for API. Web applications may be filtered based off these filter criteria. Filter criterion may include, without limitation, web application dates, web application traffic, web application types, web applications address, and the like. Once an API filters through web applications according to a filter criterion, it may select a web application. Processor 104 may transmit, through the API, user data include contextual data 108 to apparatus 100. API may further automatically fill out user entry fields of the web application with the user credentials in order to gain access to the contextual data 108. Web applications may include, without limitation, a social media website, an online form, file scanning, email programs, third party websites, governmental websites, or the like.

With continued reference to FIG. 1, processor 104 may be configured to preprocess contextual data 108. Preprocessing contextual data 108 may involve a series of steps to prepare and clean the data before it can be used for analysis, storage, or further processing. Preprocessing of contextual data 108 may include validating the contextual data 108 to ensure that it is complete, accurate, and consistent. Processor 104 may check for any missing or erroneous information and correct or flag such issues. Preprocessing a contextual data 108 may involve cleaning the data associated with the contextual data 108. This may include cleaning the data to remove any inconsistencies, outliers, duplicates, and the like. This can involve standardizing formats, dealing with missing values, and eliminating redundant or irrelevant information. In some embodiments, preprocessing the contextual data 108 may include normalizing the data to bring it to a consistent format. For instance, standardize units of measurement (e.g., pounds to kilograms) or date formats. In some cases, preprocessing the contextual data may include transforming the data into a suitable format for analysis or storage. This might include converting data into numerical values or encoding categorical variables. If contextual data 108 is collected from multiple sources, processor 104 may integrate the data into a unified dataset, mapping common identifiers to establish connections between different pieces of information. In the context of biological data, preprocessing the contextual data 108 may involve extracting specific health-related parameters or measurements, such as heart rate, blood pressure, or chemical markers. In other cases, preprocessing the contextual data 108 may include ensuring that sensitive personal and health information is properly anonymized and encrypted to protect user privacy.

With continued reference to FIG. 1, processor 104 may be configured to extract a plurality of analytical data from the contextual data 108. As used in the current disclosure, "analytical data" refers to additional information or details that provide a more comprehensive understanding of a current situation. This additional information may play a crucial role in interpreting and comprehending contextual data 108 within a specific context. Analytical data proves indispensable for precise analysis, utilization, and the extraction of insights from a dataset. This analytical data can be directly pertinent to a particular scenario, event, or entity, furnishing the necessary background and details to grasp the data's significance in that specific context. On occasion, analytical data may be employed to establish the temporal context for a user query or dataset, encompassing timestamps, time of day, day of the week, or any other time-related details that elucidate when the data was generated or its relevance to a specific moment. This may encompass the chronological sequence or timing of events or queries. Moreover, a temporal context regarding the data can be gleaned in relation to recent test and lab results. Recent laboratory test results, imaging reports, pathology results, and other diagnostic data serve to analyze the model. This analyzation empowers it to correlate symptoms with actual test findings. In an alternative scenario, the user's adherence or non-adherence to prior medical practitioner instructions can supply added context to the analytical data. This may involve particulars of medication usage, dosages, frequency, and adherence to prescribed medication plans. A clear comprehension of the user's medication regimen is crucial for providing suitable advice and considering potential interactions. In certain instances, analytical data may encompass information about a user's dietary and lifestyle choices, such as dietary habits, exercise routines, smoking or alcohol consumption, sleep patterns, and stress levels. Lifestyle factors can furnish the model with additional context for contextual data 108. For example, a user who excessively consumes alcohol or other controlled substances can shed light on issues related to the kidney, liver, and similar concerns.

With continued reference to FIG. 1, analytical data may be used to provide understanding that the user or entity associated with the data is a critical part of contextual information. This may encompass contextual data, demographics, preferences, historical interactions, and behavioral patterns. In some cases, analytical data may be specific to a user chosen profession. For example, if the user has a profession that requires them to sit at a desk (i.e. Secretary, Lawyer, Financial professional, and the like.) processor 104 may infer that the user may live a more sedimentary lifestyle as compared to a user with a non-sedimentary job (i.e. Construction Woker, Day Laborer, Professional Athlete, and the like.). When extracting the analytical data processor 104 may be configured to place the user dataset through preprocessing steps to clean, transform, and organize the data for further analysis. This could include handling missing values, standardizing formats, and converting unstructured data (e.g., text) into structured representations. In some embodiments, processor may generate contextual data as function of the metadata associated with contextual data 108.

With continued reference to FIG. 1, the processor may identify and segregate attributes the contextual data 108 that contribute to the analytical understanding of the data. For instance, it could identify temporal attributes (timestamps), spatial attributes (location data), and other user-specific contextual attributes. Processor 104 may then engage in feature engineering, where it transforms the identified attributes into features suitable for analysis. This could involve creating new features, aggregating data, or deriving statistics to capture the context effectively. Depending on the application, processor 104 may integrate external contextual data sources (e.g., weather data, contextual data, device information) to enrich the analytical understanding. This could involve querying APIs, seeding web crawlers, accessing external databases, and the like. Utilizing the extracted metadata and engineered features, the processor may perform various analyses, such as statistical analysis, machine learning modeling, or data mining, to derive insights and predictions based on the context. Processor 104 combines the insights obtained from the analysis with the identified contextual attributes and metadata to generate analytical data. This could involve creating structured representations that encapsulate both the original data and the derived insights in a way that is understandable and useful.

With continued reference to FIG. 1, processor 104 is configured to generate a query 112 as a function of contextual data 108. As used in the current disclosure a "query" is a request or question posed by apparatus 100 seeking information, assistance, or clarification on a specific topic or issue. Query 112 May be used to query a data structure, which may include a user interface data structure, which may include event handlers and the like. Query may be used to query the data structure, which may then configure a remote device to display fields, input fields, and the like to the user. Query may be used to configure remote device to receive user inputs and then generate responses to the query using user inputs. Query 112 may be formulated using words or phrases that convey what is needed. Query 112 may be delivered to the use through various mediums, including a chatbot, push notification, email, text message, website, and the like. Query 112 may be given in the form of text, images, verbally, visually, and the like. In an embodiment, query 112 may be related to one or more aspects of contextual data 108, as discussed in greater detail above. In a non-limiting example, query 112 may relate to asking for greater detail for one or more elements associated to contextual data 108. Non-limiting examples of queries that may be includes may be "describe the severity of your symptoms 1-10;" "describe your symptoms;" "how long have you had these symptoms;" "do you have pain equally on both sides of your head or just the left/right;" "do you currently smoke;" "have you ever been diagnosed with cancer;" "do you have a familial history of cancer;" "what is the cause of your injury;" "can you raise your arms above your head;" and the like. Additionally, query 112 may include asking the user to perform one or more physical tests. The physical tests may include range of motion assessments, strength testing, tenderness, and palpation testing, muscle length testing, special orthopedic tests (i.e. Lachman's test, McMurray's test, and the like), Neurological testing, balancing and proprioception testing, cardiovascular fitness testing, postural assessments, functional performance testing, pain assessment testing. In some cases, query 112 may instruct the user to place one or more medical instruments on their person to facilitate additional medical testing. This may include placing leads for an EKG or VCG, placing a blood pressure cuff to determine blood pressure. In some embodiments, a user may be instructed to place a sensor within their ear, throat, nose, reproductive organs, and the like in order to facilitate testing. Alternatively, query 112 may include inquiries related specifically to the user. For example, this may include questions regarding the caloric intake of the user for a given time period. In some cases, query 112 may be provided to the user using a digital avatar, chat bot, verbally, visually, video, and the like. Providing query 112 to the user may vary according to the symptoms or aliments of the user.

With continued reference to FIG. 1, processor 104 may generate query 112 using a query machine learning model. As used in the current disclosure, a "query machine learning model" is a machine-learning model that is configured to generate set of queries. Query machine learning model may be consistent with the machine-learning model described below in FIG. 2. Inputs to the query machine learning model may include contextual data, user data, historical versions of inquiries, non-user specific training data, contextual data, examples of inquiries and the like. Outputs to the query machine learning model may include a query. Query training data may include a plurality of data entries containing a plurality of inputs that are correlated to a plurality of outputs for training a processor by a machine-learning process. Outputs to the machine-learning process may be used as inputs for an updated machine-learning process. In an embodiment, query training data may be iteratively updated as a function of the input and output results of past query machine learning models or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

With continued reference to FIG. 1, processor 104 is configured to receive a query response 116 as a function of query 112 As used in the current disclosure, an "query response" is a response to the query that is retrieved from the remote device. Query response 116 may provide additional context or information regarding the contextual data 108. The query response may provide additional context or information regarding the contextual data 108. Query response 116 may describe in further detail any symptoms, medical tests, lifestyle factors, and the like of the user. Query response 116 may be multimodal in nature. This may include images, videos, text, audio and the like. A query response 116 may include a recording of the performance of one or more actions by the user as instructed by the query 112. This may include tasks such as performance of medical tests, submission of additional medical imaging tests, and the like. A user's submission of query responses may be recorded using at least a sensor, as mentioned herein above. The sensor may include an audiovisual capture device. In a non-limiting embodiment, query may ask a user to demonstrated their range of motion in one or more of their extremities. A possible query response to the user's query may include a video submission capturing the user demonstrating their range of motion in their extremities. Alternatively, the user can send in a voice response or text response describing the range of motion in their extremities. The query response 116 may be processed through the lens of the contextual data and can be used to provide additional context to the contextual data. This is performed with the intention of providing more tailored and accurate outputs to the user within the context of contextual data 108.

With continued reference to FIG. 1, processor 104 is configured to generate a return 120 as a function of the query response 116. As used in the current disclosure, "return" is a response to the query response. Return 120 may be computer generated response to the query response. Return 120 may be used to provide clarification to user's query response. Return 120 may be directed towards narrowing down subject of the query response. Return 120 may be used to provide a more tailored and accurate clarification of the query response.

With continued reference to FIG. 1, return 120 may be generated using a tonal adjustment engine 124. As used in the current disclose "tonal adjustment engine" is a system that tailors responses to meet an individual user's needs. An individual user's needs may be a function of the user's knowledge, education level, profession, geographic location, age, sex, emotional intelligence, and the like. In a non-limiting embodiment, the tonal adjustment engine 124 may rephrase, alter, or otherwise change return 120 to match information relating to contextual data 108. For example, if the user has a background in a medical field, tonal adjustment engine may generate responses with higher level medical vocabulary to help the user understand responses with respect to their overall knowledge of the medical field. If a user has a background in a field other than medicine, such as Law, Education, Writing, English, etc., the tonal adjustment engine may configure responses that use simpler medical vocabulary so that the user is not overwhelmed or confused by the responses generated using the tonal adjustment engine 124. Tonal adjustment engine 124 can adjust the tone of the response as a function of contextual data 108. Adjusting the tone of the response can include creating casual conversation style responses or more professional style responses, based on the user's tendencies that may be indicated in contextual data 108. In a non-limiting embodiment, tonal adjustment engine may include a default tone. As used herein, a "default tone" refers to a friendly, hospitable, and professional style of response. A default tone may include vocal characteristics that exemplify neutral pitch, volume and rhythm. In a non-limiting embodiment, tonal adjustment engine 124 may alter the default tone to match a different tone that aligns with user feedback or user responses.

With continued reference to FIG. 1, generating tonal adjustment engine 124 may comprise a tonal adjustment machine learning model 128. As used in the current disclosure, a "tonal adjustment machine learning model" is a machine-learning model that is configured to generate a tonal adjustment. As used in the current disclosure a "tonal adjustment" refers to a customization of a return as a function of a user's individual needs or preferences. Tonal adjustments may include a feed-back driven adjustment which may allow the tonal adjustments to be continuously refined based on either explicit (for example, written feedback) or implicit (inferred from the user's reactions or behavior) responses. Tonal adjustments may be tailored to resonate more effectively with an individual, which can enhance understanding of the matter. Tonal adjustment machine learning model 128 may be consistent with the machine-learning models described below in FIG. 2. Inputs to the tonal adjustment machine learning model may include contextual data 108, user data, historical versions of tonal adjustments, nonspecific user training data, analytical data, examples of tonal adjustments, and the like. Outputs of the tonal adjustment machine learning model may include a tonal adjustment tailored to contextual data 108 and the analytical data. Tonal adjustment training data may include a plurality of data entries containing a plurality of inputs that are correlated to a plurality of outputs for training the processor by a machine-learning process. In an embodiment, tonal adjustment training data may include contextual data 108 and background data as inputs correlated to examples of query 112. In a non-limiting embodiment, tonal adjustment training data may include text or blocks of text with user sentiment data in the form of data entered by users that typed text reflecting their own emotions when writing, user-entered perceptions of emotional or tonal content being expressed, implied reactions of the user to the content being expressed, historical reactions of users, and the like. The tonal adjustment training data may be collected using a web form, survey, ranking structure, and the like. In a non-limiting embodiment, the tonal adjustment training data may be recorded as an array of numerical scores per emotion, a ranking structure for users to rank their satisfaction with the generated responses, and the like. In a non-limiting embodiment, tonal adjustment training data may be collected using a Graphical User Interface (GUI), underlaying data structure, and the like. As used herein, a GUI refers to a user interface that allows users to interact with devices using at least graphical icons and visual indicators. In a non-limiting embodiment, the GUI or underlying data structure may be configured to record a specific user's reaction to text, either directly or implicitly. Tonal adjustment machine learning model 128 enhances the GUI's performance by dynamically optimizing the user experience. The tonal adjustment machine learning model continuously gauges user interactions responses, allowing the GUI to adapt more accurately and effectively. Through iterative updates and retraining, the tonal adjustment machine learning model fine-tunes its algorithms, ensuring a more intuitive and responsive interface. Obtaining directly recorded user reactions to text may include a sentiment analysis, Likert scale surveys, open-ended feedback, binary response options and the like. A sentiment analysis may allow a user to provide feedback on whether they found the responses positive, negative, or neutral. In a non-limiting embodiment, the sentiment analysis may be conducted through a rating system, detailed feedback forms and the like. A Likert scale survey may permit users to response to statements related to the responses using a scoring system that may consist of responses like strongly agree, agree, neutral, disagree, strongly disagree, and the like. Obtaining implicitly recorded user reactions may include tracking processes including, but not limited to, how quickly or slowly the user responses to prompts, length of user responses to prompts, measures of keystroke velocity, user misspellings, tone of text entered by the user, tone of user's voice responses, and the like. In a non-limiting embodiment, the direct and/or implicit user reactions to text may be associated with emotions using an emotion analysis machine learning model 140. The emotion analysis machine learning model 140 may be consistent with any machine learning models discussed throughout the disclosure. The emotional analysis machine learning model 140 may include a neural net. In a non-limiting embodiment, emotional analysis machine learning model may include a deep learning neural network, convolutional neural network, recurrent neural network, autoregressive neural network, and the like. The emotional analysis machine learning model may be a large language model, generative network, or the like. In a non-limiting embodiment, the emotional analysis machine learning model may be trained with emotional analysis training data. Emotional analysis training data may include inputs of a given category of data, such as implicit or direct user reactions, correlated to outputs, such as emotional, sentiment, tonal scores as described above. In an embodiment, outputs of the emotional analysis machine learning model correlated with associated responses may be used to retrain the tonal adjustment machine learning model 128. Tonal adjustment machine learning model may be a large language model, generative network, deep learning neural network, convolutional neural network, recurrent neural network, autoregressive neural network, and the like. Tonal adjustment training data may be received from a database. Alternatively, tonal adjustment training data may be generated using a web crawler, APO, look-up table, user input, chatbot, and the like. Tonal adjustment training data may be training data that is specific to the current user. Tonal adjustment training data may contain information about the user's contextual data, biological data, historical versions of tonal adjustments, non-user specific training data, and the like. In an embodiment, tonal adjustment machine learning model 128 may be trained with tonal adjustment training data wherein a target emotion or tone and corresponding response is inputting, and a modified text corresponding to the target emotion or tone is outputted. In an embodiment, tonal adjustment training data may be iteratively updated as a function of the input and output results of past tonal adjustment machine learning models or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

With continued reference to FIG. 1, a tonal adjustment machine learning model 128 may be generally trained using a non-user specific training data. As used in the current disclosure, "non-user specific training data" is training data comprised of a large and diverse dataset that does not contain data that is specific to the user. The non-user specific training data may be very large and describe a wide range of topics, styles, and sources. The non-user specific training data may include an excess of a billion unique words from many sources. This may include textbooks, articles, magazines, physician notes, academic papers, emails, books, websites, forums, social media, and the like. The dataset may be sourced from multiple languages to train multilingual models, encompassing major world languages. The dataset may cover various regional dialects, slangs, and idiomatic expressions to ensure a broad linguistic understanding. Additionally, the dataset may include formal and informal language, technical writing, conversational text, humor, satire, and more. The dataset may span across genres like science fiction, fantasy, mystery, romance, historical, technical, and more. The non-user specific training data may include detailed information about anatomy, physiology, biological systems, organs, and their functions, aiding in understanding the human body and its complexities. A significant portion of the dataset includes academic papers, articles, and publications from reputable medical journals. This provides the language model with a comprehensive understanding of established medical research and advancements. Non-user specific training data may include de-identified electronic health records from diverse healthcare institutions, encompassing patient demographics, medical history, symptoms, diagnoses, prescribed medications, treatments, and outcomes. The non-user specific training data may include an extensive collection of medical images such as X-rays, MRIs, CT scans, histopathology images, and other diagnostic imaging data. These images are labeled with corresponding diagnoses to help the model learn associations between visual data and medical conditions. In an embodiment, non-user specific training data may include data from clinical trials, including trial design, inclusion/exclusion criteria, treatments, outcomes, and adverse events. This data aids in understanding experimental treatments and their effects. In some cases, non-user specific training data may include pathology reports, lab test results, and other diagnostic data to help the model understand how different tests and markers relate to specific medical conditions. This may include data about pharmaceutical drugs, their mechanisms of action, dosage guidelines, side effects, contraindications, and interactions with other medications. Non-user specific training data may include a vast collection of data outlining various medical diagnoses, procedures, surgical interventions, and their associated details, aiding the model in learning disease patterns and treatment options. Non-user specific training data may include information related to genetic markers, mutations, genomic sequences, and their associations with specific diseases. This assists in understanding the genetic underpinnings of various non-user specific training data may include data associate with established healthcare guidelines, best practices, and treatment protocols followed by medical professionals in different regions or specialties.

With continued reference to FIG. 1, once processor 104 has received the non-user specific training data the dataset may undergo a preprocessing step to prepare the dataset for use in a machine learning model. This preprocessing step may be configured to remove noise, duplicates, and irrelevant content. Measures are taken to maintain the quality of the data, removing erroneous or misleading information. The preprocessing step may be configured to format and/or structure for data where the data is transformed from an unprocessed format and/or structure into a processed format and/or structure that is prepared for use in the generation and training of an artificial intelligence (AI) model, for example a machine learning model, a neural network, and the like. Preprocessing the dataset may include adding data, replicating data, and the like. In some embodiments, destructive transformation of data may include fixing or removing incorrect, corrupted, incorrectly formatted, duplicate, or incomplete data within a dataset, and the like. In some embodiments, structural transformation of data may include moving and/or combining columns of data in a data set, and the like. The converting of data may include the processing, cleansing, standardizing, and categorizing of data into a cleansed data format for use in generating an accumulated artificial intelligence (AI) model. In an embodiment, preprocessing the dataset may include the processing, cleansing, and standardizing of data into a data set and/or data bucket for use in generating an artificial intelligence model.

With continued reference to FIG. 1, processor 104 may be configured to anonymize the non-user specific training data using an anonymization process. As used in the current disclosure, an "anonymization process" is the process of anonymizing patient identifiers within the data. Anonymizing training data may be a crucial step in preserving privacy and ensuring compliance with data protection regulations such as GDPR or HIPAA when developing machine learning models. Anonymization involves removing or obfuscating personally identifiable information (PII) and sensitive data while retaining the utility and quality of the data for model training. As used in the current disclosure, "personally identifiable information" refers to information used to identify and distinguish individual patients in healthcare records and systems. PII may include any identifiers described in the Health Insurance Portability and Accountability Act (HIPAA). Examples of PII include the name, address, phone number, email address, phone number, email address, social security number (SSN), national identification number, medical record number, health insurance information, beneficiary information, account numbers, and the like. Processor 104 may be configured to anonymize each patient identifier within the non-user specific training data and/or the tonal adjustment training data to ensure that no patient can be identified based on this data. In an embodiment, an anonymization processes may include redacting the patient identifiers within the non-user specific training data and/or the query training data. Redacting may be done using various methods like blacking out, using placeholders, or applying software tools to mask or replace the sensitive data. In an embodiment, this may involve removing or replacing patient identifiers with pseudonyms and/or generic terms. In another embodiment, the anonymization process may replace PII with pseudonyms or tokens. For example, processor 104 may replace names with unique identifiers, such as "User12345," and email addresses with placeholders like user@email.com. In some cases, processor 104 may group data into broader categories to reduce the granularity of information. For instance, processor 104 can generalize ages into age groups (e.g., 20-30, 31-40) rather than using exact ages. In some cases, anonymization process may Create synthetic data that mimics the statistical properties of the original data. This can help maintain data utility while preventing re-identification.

With continued reference to FIG. 1, processor 104 may be configured to place the non-user specific training data through a verification process. As used in the current disclosure, a "verification process" is a process targeted at verifying the accuracy and authenticity of training data. In an embodiment, the verification process may verify the source of the non-user specific training data. This may be done to ensure that the origins of the training data are from trustworthy sources which thereby improves the trustworthiness of the entire dataset. A verification process may additionally data cleaning to identify and rectify errors, inconsistencies, missing values, and outliers within the training data. This may include the use of domain expertise and specialized tools to ensure the data is in a usable format. In some cases, the verification process may identify portions of the non-user specific training data that processor 104 has low confidence in. Those portions of training data may then be presented to healthcare professionals, clinicians, and subject matter experts to review the data. Their domain knowledge may be crucial in assessing the relevance and accuracy of the training data. They then can validate whether the data aligns with medical standards and guidelines. In some cases, the verification process may identify low-confidence portions of the non-user specific training data by cross-reference the non-user specific training data with established databases, published literature, or official medical records to validate its accuracy. Ensure that the data aligns with existing validated information. If the low-confidence portions of the non-user specific training data are proven to be invalid by processor 104 and/or a medical practitioner, those portions of the training data may be removed.

Still referring to FIG. 1, a tonal adjustment machine learning model 128 may include a large language model (LLM). A "large language model," as used herein, is a deep learning algorithm that can recognize, summarize, translate, predict and/or generate text and other content based on knowledge gained from massive datasets. Large language model may be trained on large sets of data; for example, non-user specific training data. Training sets may be drawn from diverse sets of data such as, as non-limiting examples, novels, blog posts, articles, emails, contextual data 108, and the like. In some embodiments, training sets may include a variety of subject matters, such as, as nonlimiting examples, medical report documents, electronic health records, entity documents, business documents, inventory documentation, emails, user communications, advertising documents, newspaper articles, and the like. In some embodiments, training sets of LLM 132 may include a plurality of contextual data 108. In some embodiments, training sets of LLM 132 may include information from one or more public or private databases. As a non-limiting example, training sets may include databases associated with an entity. In some embodiments, training sets may include portions of documents associated with contextual data 108 correlated to examples of queries. In an embodiment, LLM 132 may include one or more architectures based on the task requirements of LLM 132. Common architectures may include GPT (Generative Pretrained Transformer), BERT (Bidirectional Encoder Representations from Transformers), T5 (Text-To-Text Transfer Transformer), etc. The architecture choice depends on whether you need generative, contextual, or other specific capabilities.

With continued reference to FIG. 1, in some embodiments, LLM 132 may be generally trained. For the purposes of this disclosure, "generally trained" means that LLM 132 is trained on a general training set comprising a variety of subject matters, data sets, and fields. In some embodiments, LLM 132 may be initially generally trained. In some embodiments, for the purposes of this disclosure, LLM 132 may be specifically trained. For the purposes of this disclosure, "specifically trained" means that LLM 132 is trained on a specific training set, wherein the specific training set includes data including specific correlations for LLM 132 to learn. As a non-limiting example, LLM 132 may be generally trained on a general training set, then specifically trained on a specific training set. In an embodiment, specific training of the LLM 132 may be performed using a supervised machine learning process. Whereas, generally training the LLM 132 may be performed using an unsupervised machine learning process. As a non-limiting example, specific training set may include examples of comprehensive reports. As a non-limiting example, specific training set may include scholastic works. As a non-limiting example, specific training set may include information from a database. As a non-limiting example, specific training set may include text related to the users such as user specific data and contextual data extracted from the user specific data correlated to examples of a tonal adjustment machine learning model 128. In an embodiment, training the tonal adjustment machine learning model 128 may include setting the parameters of the model (weights and biases) either randomly or using a pretrained model. Generally training the tonal adjustment machine learning model 128 on a large corpus of text data can provide a starting point for fine-tuning on the specific task. The model may learn by adjusting its parameters during the training process to minimize a defined loss function, which measures the difference between predicted outputs and ground truth. Once the model has been generally trained, the model may then be specifically trained to fine-tune the pretrained model on task-specific data to adapt it to the target task. Fine-tuning involves training the model with user-specific training data, adjusting the model's weights to optimize performance for the particular task. In some cases, this may include optimizing the model's performance by fine-tuning hyperparameters such as learning rate, batch size, and regularization. Hyperparameter tuning helps in achieving the best performance and convergence during training.

With continued reference to FIG. 1, LLM 132, in some embodiments, may include Generative Pretrained Transformer (GPT), GPT-2, GPT-3, GPT-4, and the like. GPT, GPT-2, GPT-3, GPT-3.5, and GPT-4 are products of Open AI Inc., of San Francisco, CA. LLM 132 may include a text prediction based algorithm configured to receive an article and apply a probability distribution to the words already typed in a sentence to work out the most likely word to come next in augmented articles. For example, if the words already typed are "Nice to meet", then it is highly likely that the word "you" will come next. LLM 132 may output such predictions by ranking words by likelihood or a prompt parameter. For the example given above, the LLM 132 may score "you" as the most likely, "your" as the next most likely, "his" or "her" next, and the like. LLM 132 may include an encoder component and a decoder component.

Still referring to FIG. 1, LLM 132 may include a transformer architecture. In some embodiments, encoder component of LLM 132 may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. "Positional encoding," for the purposes of this disclosure, refers to a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIG. 1, LLM 132 and/or transformer architecture may include an attention mechanism. An "attention mechanism," as used herein, is a part of a neural architecture that enables a system to dynamically quantify the relevant features of the input data. In the case of natural language processing, input data may be a sequence of textual elements. It may be applied directly to the raw input or to its higher-level representation.

With continued reference to FIG. 1, an attention mechanism may represent an improvement over a limitation of the Encoder-Decoder model. The encoder-decoder model encodes the input sequence to one fixed length vector from which the output is decoded at each time step. This issue may be seen as a problem when decoding long sequences because it may make it difficult for the neural network to cope with long sentences, such as those that are longer than the sentences in the training corpus. Applying an attention mechanism, LLM 132 may predict the next word by searching for a set of positions in a source sentence where the most relevant information is concentrated. LLM 132 may then predict the next word based on context vectors associated with these source positions and all the previously generated target words, such as textual data of a dictionary correlated to a prompt in a training data set. A "context vector," as used herein, are fixed-length vector representations useful for document retrieval and word sense disambiguation.

Still referring to FIG. 1, an attention mechanism may include generalized attention self-attention, multi-head attention, additive attention, global attention, and the like. In generalized attention, when a sequence of words or an image is fed to LLM 132, it may verify each element of the input sequence and compare it against the output sequence. Each iteration may involve the mechanism's encoder capturing the input sequence and comparing it with each element of the decoder's sequence. From the comparison scores, the mechanism may then select the words or parts of the image that it needs to pay attention to. In self-attention, LLM 132 may pick up particular parts at different positions in the input sequence and over time compute an initial composition of the output sequence. In multi-head attention, LLM 132 may include a transformer model of an attention mechanism. Attention mechanisms, as described above, may provide context for any position in the input sequence. For example, if the input data is a natural language sentence, the transformer does not have to process one word at a time. In multi-head attention, computations by LLM 132 may be repeated over several iterations, each computation may form parallel layers known as attention heads. Each separate head may independently pass the input sequence and corresponding output sequence element through a separate head. A final attention score may be produced by combining attention scores at each head so that every nuance of the input sequence is taken into consideration. In additive attention (Bahdanau attention mechanism), LLM 132 may make use of attention alignment scores based on a number of factors. These alignment scores may be calculated at different points in a neural network. Source or input sequence words are correlated with target or output sequence words but not to an exact degree. This correlation may take into account all hidden states and the final alignment score is the summation of the matrix of alignment scores. In global attention (Luong mechanism), in situations where neural machine translations are required, LLM 132 may either attend to all source words or predict the target sentence, thereby attending to a smaller subset of words.

With continued reference to FIG. 1, multi-headed attention in encoder may apply a specific attention mechanism called self-attention. Self-attention allows the models to associate each word in the input, to other words. So, as a non-limiting example, the LLM 132 may learn to associate the word "you", with "how" and "are". It's also possible that LLM 132 learns that words structured in this pattern are typically a question and to respond appropriately. In some embodiments, to achieve self-attention, input may be fed into three distinct fully connected layers to create query, key, and value vectors. The query, key, and value vectors may be fed through a linear layer; then, the query and key vectors may be multiplied using dot product matrix multiplication in order to produce a score matrix. The score matrix may determine the amount of focus for a word should be put on other words (thus, each word may be a score that corresponds to other words in the time-step). The values in score matrix may be scaled down. As a non-limiting example, score matrix may be divided by the square root of the dimension of the query and key vectors. In some embodiments, the softmax of the scaled scores in score matrix may be taken. The output of this softmax function may be called the attention weights. Attention weights may be multiplied by your value vector to obtain an output vector. The output vector may then be fed through a final linear layer.

With continued reference to FIG. 1, in order to use self-attention in a multi-headed attention computation, query, key, and value may be split into N vectors before applying self-attention. Each self-attention process may be called a "head." Each head may produce an output vector and each output vector from each head may be concatenated into a single vector. This single vector may then be fed through the final linear layer discussed above. In theory, each head can learn something different from the input, therefore giving the encoder model more representation power.

With continued reference to FIG. 1, encoder of transformer may include a residual connection. Residual connection may include adding the output from multi-headed attention to the positional input embedding. In some embodiments, the output from residual connection may go through a layer normalization. In some embodiments, the normalized residual output may be projected through a pointwise feed-forward network for further processing. The pointwise feed-forward network may include a couple of linear layers with a ReLU activation in between. The output may then be added to the input of the pointwise feed-forward network and further normalized.

With continued reference to FIG. 1, transformer architecture may include a decoder. Decoder may a multi-headed attention layer, a pointwise feed-forward layer, one or more residual connections, and layer normalization (particularly after each sub-layer), as discussed in more detail above. In some embodiments, decoder may include two multi-headed attention layers. In some embodiments, decoder may be autoregressive. For the purposes of this disclosure, "autoregressive" means that the decoder takes in a list of previous outputs as inputs along with encoder outputs containing attention information from the input.

With continued reference to FIG. 1, in some embodiments, input to decoder may go through an embedding layer and positional encoding layer in order to obtain positional embeddings. Decoder may include a first multi-headed attention layer, wherein the first multi-headed attention layer may receive positional embeddings.

With continued reference to FIG. 1, first multi-headed attention layer may be configured to not condition to future tokens. As a non-limiting example, when computing attention scores on the word "am," decoder should not have access to the word "fine" in "I am fine," because that word is a future word that was generated after. The word "am" should only have access to itself and the words before it. In some embodiments, this may be accomplished by implementing a look-ahead mask. Look ahead mask is a matrix of the same dimensions as the scaled attention score matrix that is filled with "0s" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when the softmax of this matrix is taken, the negative infinities will be zeroed out; this leaves zero attention scores for "future tokens."

With continued reference to FIG. 1, second multi-headed attention layer may use encoder outputs as queries and keys and the outputs from the first multi-headed attention layer as values. This process matches the encoder's input to the decoder's input, allowing the decoder to decide which encoder input is relevant to put a focus on. The output from second multi-headed attention layer may be fed through a pointwise feedforward layer for further processing.

With continued reference to FIG. 1, the output of the pointwise feedforward layer may be fed through a final linear layer. This final linear layer may act as a classifier. This classifier may be as big as the number of classes that you have. For example, if you have 10,000 classes for 10,000 words, the output of that classifier will be of size 10,000. The output of this classifier may be fed into a softmax layer which may serve to produce probability scores between zero and one. The index may be taken of the highest probability score in order to determine a predicted word.

With continued reference to FIG. 1, decoder may take this output and add it to the decoder inputs. Decoder may continue decoding until a token is predicted. Decoder may stop decoding once it predicts an end token.

With continued reference to FIG. 1, in some embodiment, decoder may be stacked N layers high, with each layer taking in inputs from the encoder and layers before it. Stacking layers may allow LLM 132 to learn to extract and focus on different combinations of attention from its attention heads.

With continued reference to FIG. 1, LLM 132 may receive an input. Input may include a string of one or more characters, such as contextual data 108 and analytical data. Inputs may additionally include query 112. For example, input may include one or more words, a sentence, a paragraph, a thought, a query, and the like. A "query" for the purposes of the disclosure is a string of characters that poses a question. In some embodiments, input may be received from a user device. User device may be any computing device that is used by a user. As non-limiting examples, user device may include desktops, laptops, smartphones, tablets, and the like. Query may include, for example a question asking for a status update regarding a to-do list. In some embodiments, input may include a set of background data associated with contextual data 108.

With continued reference to FIG. 1, LLM 132 may generate query 112 as an output. In some embodiments, LLM 132 may include multiple sets of transformer architecture as described above. Output may include a textual output. A "textual output," for the purposes of this disclosure is an output comprising a string of one or more characters. Textual output may include, for example, a comprehensive report. In some embodiments, textual output may include a phrase or sentence identifying the status of a user query. In some embodiments, textual output may include a sentence or plurality of sentences describing a response to a user query. As a non-limiting example, this may include restrictions, timing, advice, dangers, benefits, and the like.

With continued reference to FIG. 1, machine learning plays a crucial role in enhancing the function of software for generating a tonal adjustment machine learning model 128. This may include identifying patterns within contextual data 108 that lead to changes in the capabilities and type of the tonal adjustment machine learning model 128. By analyzing vast amounts of data related to biological data, machine learning algorithms can identify patterns, correlations, and dependencies that contribute to generating the tonal adjustment machine learning model 128. These algorithms can extract valuable insights from various sources, including text, document, audio, and other multimodal data associated with the contextual data 108. By applying machine learning techniques, the software can generate the tonal adjustment machine learning model 128 extremely accurately. Machine learning models may enable the software to learn from past collaborative experiences of the entities and iteratively improve its training data over time.

With continued reference to FIG. 1, processor 104 may be configured to update the training data of the tonal adjustment machine learning model 128 using user inputs. Tonal adjustment machine learning model 128 may use user input to update its training data, thereby improving its performance and accuracy. In embodiments, the tonal adjustment machine learning model 128 may be iteratively updated using input and output results of the tonal adjustment machine learning model 128. The tonal adjustment machine learning model 128 may then be iteratively retrained using the updated machine-learning model. For instance, and without limitation, tonal adjustment machine learning model 128 may be trained using a first training data from, for example, and without limitation, training data from a user input or database. The tonal adjustment machine learning model 128 may then be updated by using previous inputs and outputs from the tonal adjustment machine learning model 128 as second training data to then train a second machine learning model or a second iteration of the tonal adjustment machine learning model 128. This process of updating the tonal adjustment machine learning model 128 may be continuously done to create subsequent a second set of responses which may be used to prompt the user to provide a second set of query responses. The second set of query responses may be used as training data for specifically training the tonal adjustment machine-learning model 128. When users interact with the software, their actions, preferences, and feedback provide valuable information that can be used to refine and enhance the model. This user input is collected and incorporated into the training data, allowing the machine learning model to learn from real-world interactions and adapt its predictions accordingly. By continually incorporating user input, the model becomes more responsive to user needs and preferences, capturing evolving trends and patterns. This iterative process of updating the training data with user input enables the machine learning model to deliver more personalized and relevant results, ultimately enhancing the overall user experience. The discussion within this paragraph may apply to both the tonal adjustment machine learning model 128 and/or any other machine-learning model/classifier discussed herein. Tonal adjustment machine learning model may aid in adaptive communication which can modify the style or method of communication based on historical tonal adjustment data, user's feedback, behavior, expressed needs, implied needs, or the like. In a non-limiting embodiment, generation of a tonal adjustment may be achieved through a single machine learning model, neural network, or by stages or layers of the machine learning model or neural network. For example, the neural network may include initial layers or stages for semantic processing, meaning creating an accurate return with respect to definitions and explanations of the phrases, followed by layers or stages for "tonal" processing or adjustment, as discussed above.

Incorporating the user feedback may include updating the training data by removing or adding correlations of user data to a path or resources as indicated by the feedback. Any machine-learning model as described herein may have the training data updated based on such feedback or data gathered using a web crawler as described above. For example, correlations in training data may be based on outdated information wherein, a web crawler may update such correlations based on more recent resources and information.

With continued reference to FIG. 1, processor 104 may use user feedback to train the machine-learning models and/or classifiers described above. For example, machine-learning models and/or classifiers may be trained using past inputs and outputs of classifier. In some embodiments, if user feedback indicates that an output of classifier was "bad," then that output and the corresponding input may be removed from training data used to train machine-learning models and/or classifiers, and/or may be replaced with a value entered by, e.g., another value that represents an ideal output given the input the machine learning model originally received, permitting use in retraining, and adding to training data; in either case, machine learning models and/or classifiers may be retrained with modified training data as described in further detail below. In some embodiments, training data of classifier may include user feedback.

With continued reference to FIG. 1, in some embodiments, an accuracy score may be calculated for classifier using user feedback. For the purposes of this disclosure, "accuracy score," is a numerical value concerning the accuracy of a machine-learning model. For example, the accuracy/quality of the output tonal adjustment machine learning model 128 may be averaged to determine an accuracy score. In some embodiments, an accuracy score may be determined for pairing of entities. Accuracy score or another score as described above may indicate a degree of retraining needed for a machine-learning model such as a classifier; processor 104 may perform a larger number of retraining cycles for a higher number (or lower number, depending on a numerical interpretation used), and/or may collect more training data for such retraining. The discussion within this paragraph and the paragraphs preceding this paragraph may apply to both the tonal adjustment machine learning model 128 and/or any other machine-learning model/classifier mentioned herein.

With continued reference to FIG. 1, in one or more embodiments, processor 104 may implement one or more aspects of "generative artificial intelligence (AI)," a type of AI that uses machine learning algorithms to create, establish, or otherwise generate data such as, without limitation, user score or comprehensive report and/or the like in any data structure as described herein (e.g., text, image, video, audio, among others) that is similar to one or more provided training examples. In an embodiment, machine learning module described herein may generate one or more generative machine learning models that are trained on one or more set of event training data and/or report training data. One or more generative machine learning models may be configured to generate new examples that are similar to the training data of the one or more generative machine learning models but are not exact replicas; for instance, and without limitation, data quality or attributes of the generated examples may bear a resemblance to the training data provided to one or more generative machine learning models, wherein the resemblance may pertain to underlying patterns, features, or structures found within the provided training data.

Still referring to FIG. 1, in some cases, generative machine learning models may include one or more generative models. As described herein, "generative models" refers to statistical models of the joint probability distribution P(X, Y) on a given observable variable x, representing features or data that can be directly measured or observed (e.g. contextual data 108 and contextual data) and target variable y, representing the outcomes or labels that one or more generative models aims to predict or generate (e.g., an query machine learning model 124). In some cases, generative models may rely on Bayes theorem to find joint probability; for instance, and without limitation, Naïve Bayes classifiers may be employed by processor 104 to categorize input data such as, without limitation the contextual data and the contextual data 108 into the first set of inquiries 116 and/or second set of inquiries 120.

In a non-limiting example, and still referring to FIG. 1, one or more generative machine learning models may include one or more Naïve Bayes classifiers generated, by processor 104, using a Naïve bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)=P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction.

Still referring to FIG. 1, although Naïve Bayes classifier may be primarily known as a probabilistic classification algorithm; however, it may also be considered a generative model described herein due to its capability of modeling the joint probability distribution P(X, Y) over observable variables X and target variable Y. In an embodiment, Naïve Bayes classifier may be configured to make an assumption that the features X are conditionally independent given class label Y, allowing generative model to estimate the joint distribution as P(X, Y)=P(Y)ΠiP(Xi|Y), wherein P(Y) may be the prior probability of the class, and P($X_i$|Y) is the conditional probability of each feature given the class. One or more generative machine learning models containing Naïve Bayes classifiers may be trained on labeled training data, estimating conditional probabilities P($X_i$|Y) and prior probabilities P(Y) for each class; for instance, and without limitation, using techniques such as Maximum Likelihood Estimation (MLE). One or more generative machine learning models containing Naïve Bayes classifiers may select a class label y according to prior distribution P(Y), and for each feature Xi, sample at least a value according to conditional distribution P($X_i$|y). Sampled feature values may then be combined to form one or more new data instance with selected class label y. In a non-limiting example, one or more generative machine learning models may include one or more Naïve Bayes classifiers to generate new examples of a comprehensive reports and/or a user score based on inputs as described herein, wherein the models may be trained using training data containing a plurality of features, and/or the like as input correlated to a plurality of labeled classes.

Still referring to FIG. 1, in some cases, one or more generative machine learning models may include generative adversarial network (GAN). As used in this disclosure, a "generative adversarial network" is a type of artificial neural network with at least two sub models (e.g., neural networks), a generator, and a discriminator, that compete against each other in a process that ultimately results in the generator learning to generate new data samples, wherein the "generator" is a component of the GAN that learns to create hypothetical data by incorporating feedbacks from the "discriminator" configured to distinguish real data from the hypothetical data. In some cases, generator may learn to make discriminator classify its output as real. In an embodiment, discriminator may include a supervised machine learning model while generator may include an unsupervised machine learning model as described in further detail with reference to FIG. 2.

With continued reference to FIG. 1, in an embodiment, discriminator may include one or more discriminative models, i.e., models of conditional probability P(Y|X=x) of target variable Y, given observed variable X. In an embodiment, discriminative models may learn boundaries between classes or labels in given training data. In a non-limiting example, discriminator may include one or more classifiers as described in further detail below with reference to FIG. 2 to distinguish between different categories, or states e.g., TRUE vs. FALSE within the context of generated data such as, without limitations, a comprehensive report and/or a user score, and/or the like. In some cases, processor 104 may implement one or more classification algorithms such as, without limitation, Support Vector Machines (SVM), Logistic Regression, Decision Trees, and/or the like to define decision boundaries.

Still referring to FIG. 1, processor 104 may be configured to display return 120 using display device 136. As used in the current disclosure, a "display device" is a device that is used to display a plurality of data and other digital content. A display device 136 may include a user interface. A "user interface," as used herein, is a means by which a user and a computer system interact, for example through the use of input devices and software. A user interface may include a graphical user interface (GUI), command line interface (CLI), menu-driven user interface, touch user interface, voice user interface (VUI), form-based user interface, any combination thereof, and the like. A user interface may include a smartphone, smart tablet, desktop, or laptop operated by the user. In an embodiment, the user interface may include a graphical user interface. In some embodiments, GUI may include icons, menus, other visual indicators, or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pulldown menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access. Information contained in user interface may be directly influenced using graphical control elements such as widgets. A "widget," as used herein, is a user control element that allows a user to control and change the appearance of elements in the user interface. In this context a widget may refer to a generic GUI element such as a check box, button, or scroll bar to an instance of that element, or to a customized collection of such elements used for a specific function or application (such as a dialog box for users to customize their computer screen appearances). User interface controls may include software components that a user interacts with through direct manipulation to read or edit information displayed through user interface. Widgets may be used to display lists of related items, navigate the system using links, tabs, and manipulate data using check boxes, radio boxes, and the like.

Figure 2:
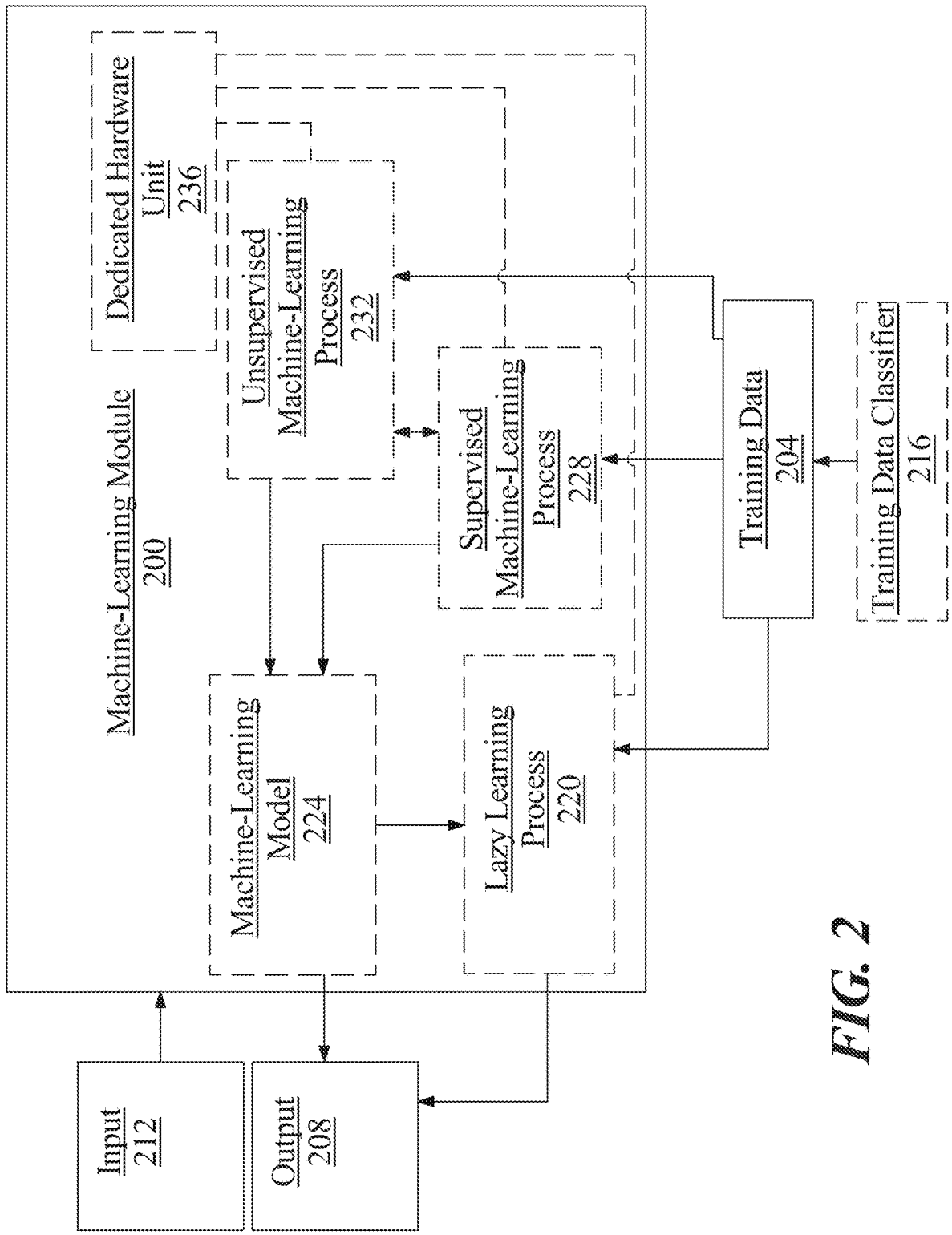
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process,"

as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example, contextual data 108 as inputs correlated to a first set of inquiries 116 as outputs.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to elements of biological data to examples of diagnostic data.

With further reference to FIG. 2, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or another device, or the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively, or additionally, one or more training examples may identify as having poor quality data, where "poor quality" is defined as having a signal to noise ratio below a threshold value.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity, and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include contextual data 108 as described above as inputs, a first set of user inquiries 116 as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 232 may not require a response variable; unsupervised processes 232 may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized, or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 236. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 236 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 236 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 236 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 3:
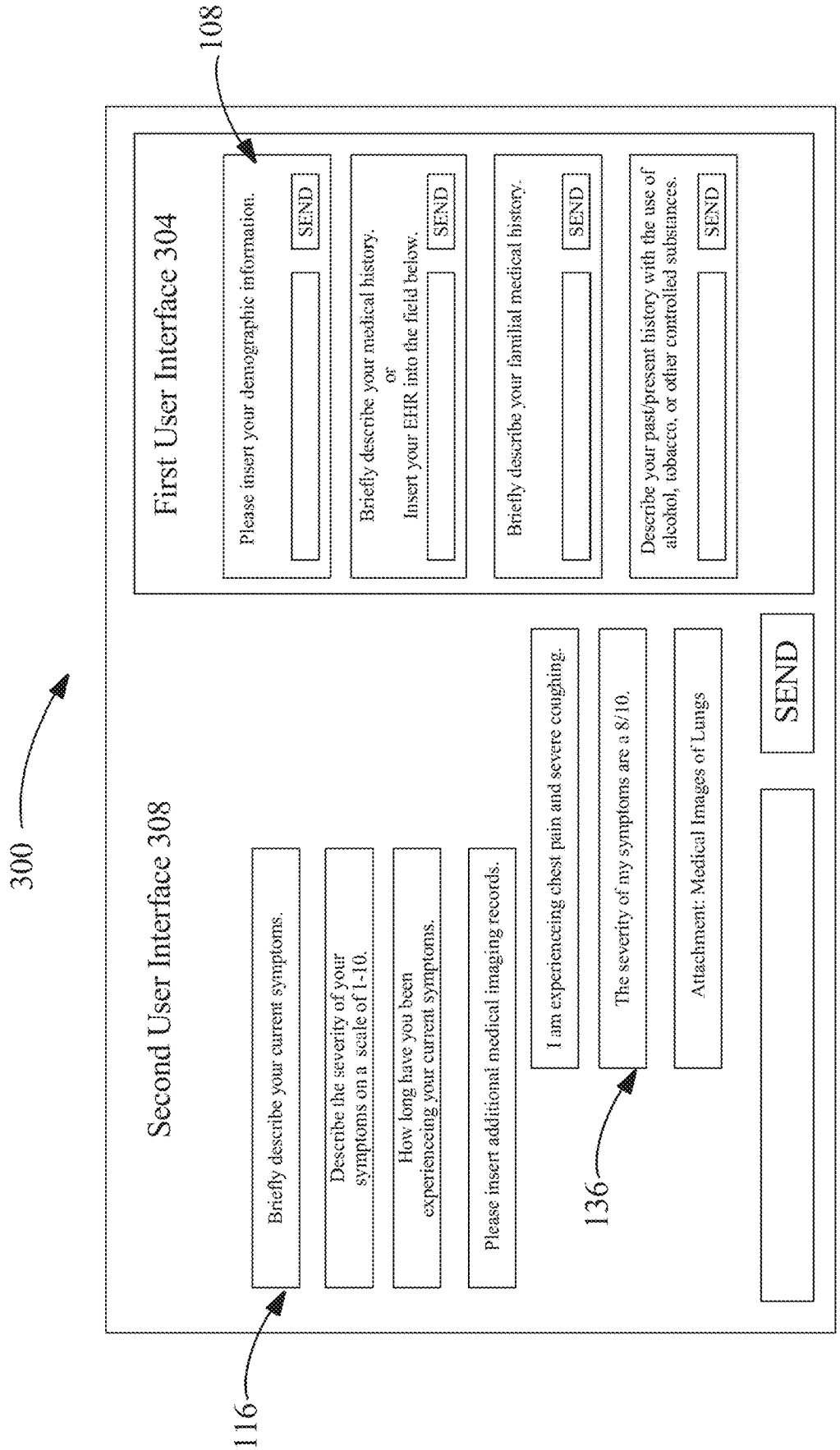
FIG. 3 is an illustration of an exemplary embodiment of a plurality of user interfaces.

Referring now to FIG. 3, an exemplary embodiment of a plurality of user interfaces. As used in the current disclosure, a "user interface" is the point of interaction between a user and a digital system or device. A user interface may include elements and mechanisms that enable users to interact with and control the system, application, or software in a visually understandable and intuitive manner. The primary goal of a user interface is to enhance user experience by presenting information in a clear, efficient, and aesthetically pleasing way. FIG. 3 depicts at least two distinct user interfaces, a first user interface 304 and a second user interface 308, respectively. The first user interface 304 may be configured to allow the user to submit information associated with the contextual data 108 via one or more input fields. Input fields may include text boxes, dropdown menus, buttons, icons, and the like. The input fields of the first user interface 304 may allow the user to submit text, images, audio, documents, video, and the like. The first user interface 304 may allow the user to submit, adjust, or modify portions of the contextual data 108, The second user interface 308 may take the form of a chatbot, as discussed in greater detail herein below, to submit the first set of inquiries and/or the second set of inquiries to the user. Additionally, the second user interface 308 may allow the user to respond to the first set of queries and/or the second set of queries using the first set of query responses and/or second set of query responses. The user may submit the first set of query responses and/or second set of query responses using one or more input fields. In some cases, the second user interface 308 may be communicatively connected to at least a sensor. The sensor may be configured to allow the user to record video, audio, and the like as the first set of query responses and/or second set of query responses. In an embodiment, a user may be connected via audio or video call to a medical professional through a user interface. Apparatus 100 may connect the user based on the results contained in the user report or contextual data 108.

Figure 4:
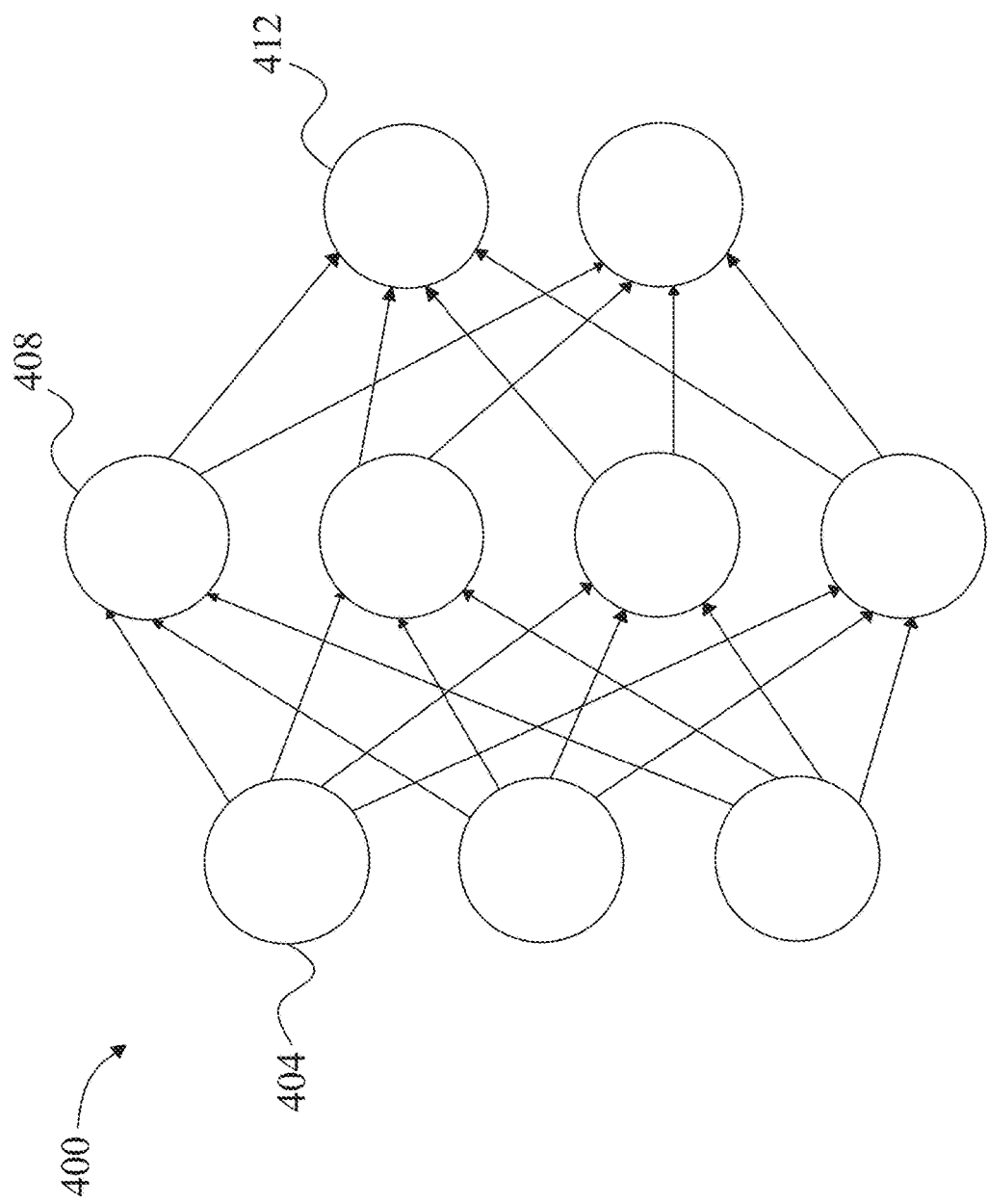
FIG. 4 is a diagram of an exemplary embodiment of a neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
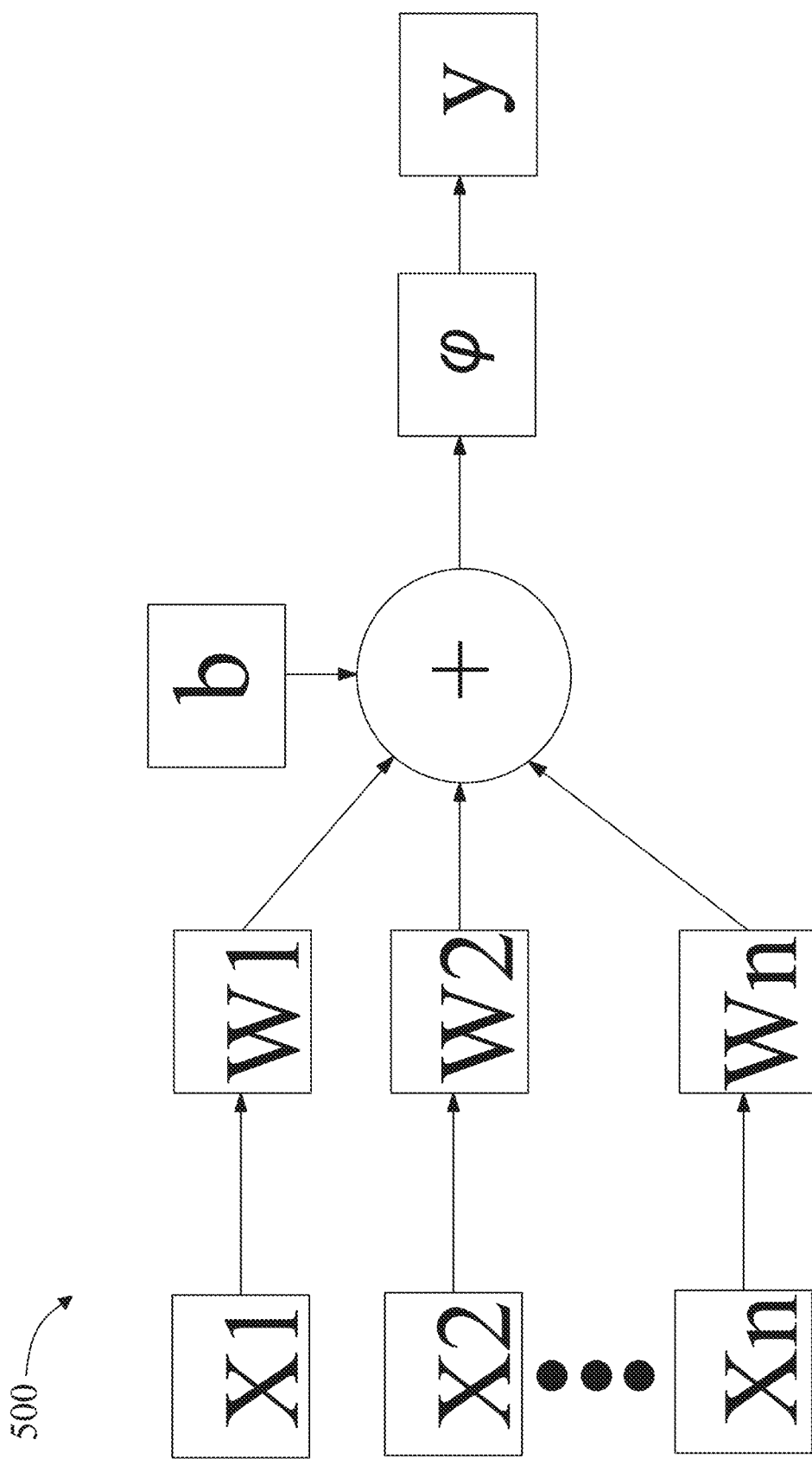
FIG. 5 is a diagram of an exemplary embodiment of a node of a neural network.

Referring now to FIG. 5, an exemplary embodiment of a node of a neural network is illustrated. A node may include, without limitation, a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 6:
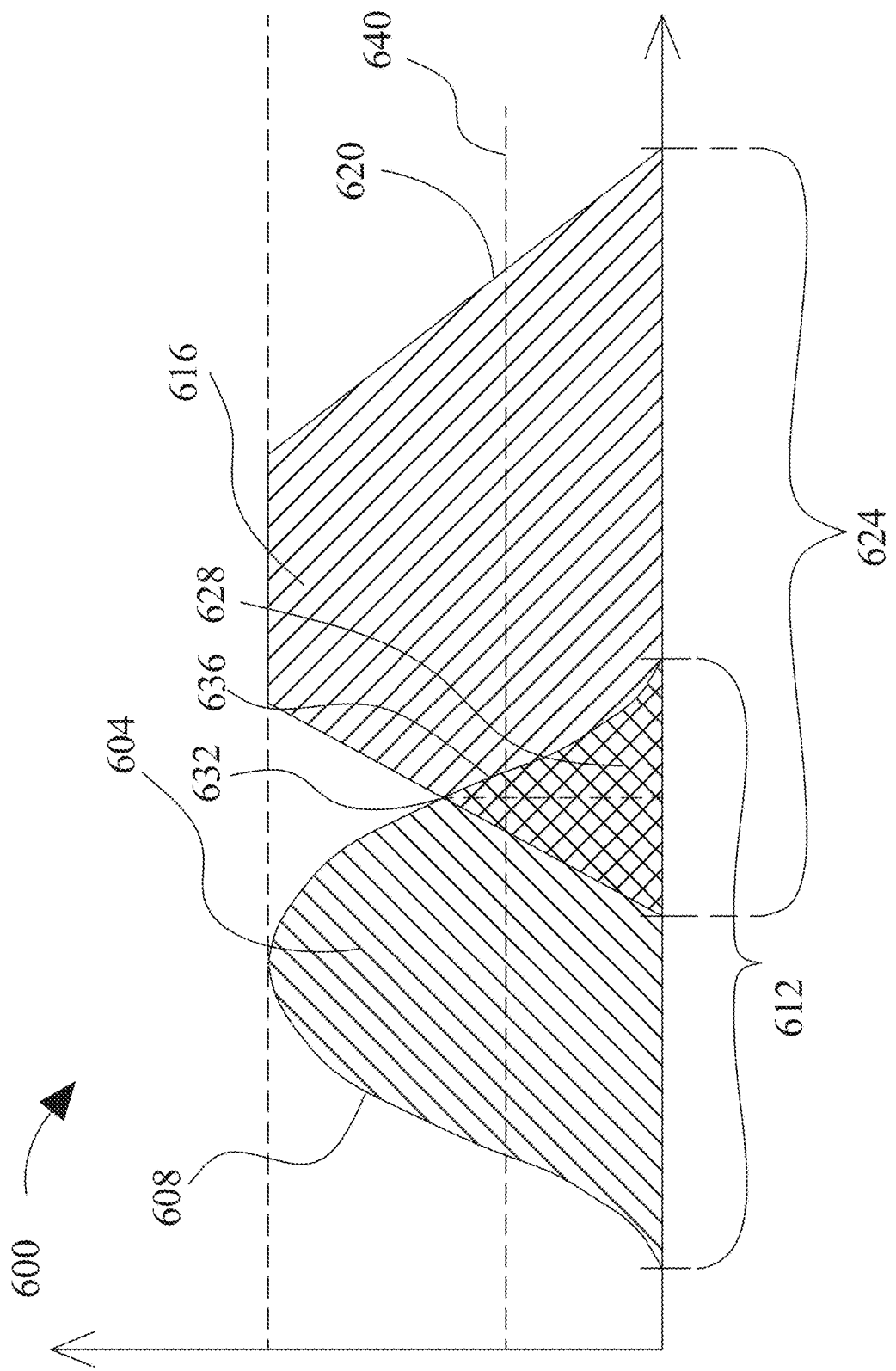
FIG. 6 is an illustration of an exemplary embodiment of fuzzy set comparison.

Now referring to FIG. 6, an exemplary embodiment of fuzzy set comparison 600 is illustrated. In a non-limiting embodiment, the fuzzy set comparison. In a non-limiting embodiment, fuzzy set comparison 600 may be consistent with fuzzy set comparison in FIG. 1. In another non-limiting the fuzzy set comparison 600 may be consistent with the name/version matching as described herein. For example and without limitation, the parameters, weights, and/or coefficients of the membership functions may be tuned using any machine-learning methods for the name/version matching as described herein. In another non-limiting embodiment, the fuzzy set may represent contextual data 108 and query response data from FIG. 1.

Alternatively or additionally, and still referring to FIG. 6, fuzzy set comparison 600 may be generated as a function of determining the data compatibility threshold. The compatibility threshold may be determined by a computing device. In some embodiments, a computing device may use a logic comparison program, such as, but not limited to, a fuzzy logic model to determine the compatibility threshold and/or version authenticator. Each such compatibility threshold may be represented as a value for a posting variable representing the compatibility threshold, or in other words a fuzzy set as described above that corresponds to a degree of compatibility and/or allowability as calculated using any statistical, machine-learning, or other method that may occur to a person skilled in the art upon reviewing the entirety of this disclosure. In some embodiments, determining the compatibility threshold and/or version authenticator may include using a linear regression model. A linear regression model may include a machine learning model. A linear regression model may map statistics such as, but not limited to, frequency of the same range of version numbers, and the like, to the compatibility threshold and/or version authenticator. In some embodiments, determining the compatibility threshold of any posting may include using a classification model. A classification model may be configured to input collected data and cluster data to a centroid based on, but not limited to, frequency of appearance of the range of versioning numbers, linguistic indicators of compatibility and/or allowability, and the like. Centroids may include scores assigned to them such that the compatibility threshold may each be assigned a score. In some embodiments, a classification model may include a K-means clustering model. In some embodiments, a classification model may include a particle swarm optimization model. In some embodiments, determining a compatibility threshold may include using a fuzzy inference engine. A fuzzy inference engine may be configured to map one or more compatibility thresholds using fuzzy logic. In some embodiments, a plurality of computing devices may be arranged by a logic comparison program into compatibility arrangements. A "compatibility arrangement" as used in this disclosure is any grouping of objects and/or data based on skill level and/or output score. Membership function coefficients and/or constants as described above may be tuned according to classification and/or clustering algorithms. For instance, and without limitation, a clustering algorithm may determine a Gaussian or other distribution of questions about a centroid corresponding to a given compatibility threshold and/or version authenticator, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Still referring to FIG. 6, inference engine may be implemented according to input contextual data 108 and query response data. For instance, an acceptance variable may represent a first measurable value pertaining to the classification of contextual data to query response data. Continuing the example, an output variable may represent diagnostic data associated with the user. In an embodiment, contextual data 108 and/or query response data may be represented by their own fuzzy set. In other embodiments, the classification of the data into diagnostic data may be represented as a function of the intersection two fuzzy sets as shown in FIG. 6, An inference engine may combine rules, such as any semantic versioning, semantic language, version ranges, and the like thereof. The degree to which a given input function membership matches a given rule may be determined by a triangular norm or "T-norm" of the rule or output function with the input function, such as min (a, b), product of a and b, drastic product of a and b, Hamacher product of a and b, or the like, satisfying the rules of commutativity (T(a, b)=T(b, a)), monotonicity: (T(a, b)≤T(c, d) if a≤c and b≤d), (associativity: T(a, T(b, c))=T(T(a, b), c)), and the requirement that the number 1 acts as an identity element. Combinations of rules ("and" or "or" combination of rule membership determinations) may be performed using any T-conorm, as represented by an inverted T symbol or "⊥," such as max(a, b), probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively or additionally, output rules may be replaced with functions according to the Takagi-Sugeno-King (TSK) fuzzy model.

A first fuzzy set 604 may be represented, without limitation, according to a first membership function 608 representing a probability that an input falling on a first range of values 612 is a member of the first fuzzy set 604, where the first membership function 608 has values on a range of probabilities such as without limitation the interval [0,1], and an area beneath the first membership function 608 may represent a set of values within first fuzzy set 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range 612 to a probability interval, including without limitation a triangular function defined by two linear elements such as line segments or planes that intersect at or below the top of the probability interval. As a non-limiting example, triangular membership function may be defined as:

$$(x, a, b, c) = \begin{cases} 0, \text{ for } x > c \text{ and } x < a \\ \frac{x-a}{b-a}, \text{ for } a \le x < b \\ \frac{c-x}{c-b}, \text{ if } b < x \le c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}(\frac{x-c}{\sigma})^2}$$

and a bell membership function may be defined as:

$$y(x, a, b, c) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

First fuzzy set 604 may represent any value or combination of values as described above, including any biological data and diagnostic data. A second fuzzy set 616, which may represent any value which may be represented by first fuzzy set 604, may be defined by a second membership function 620 on a second range 624; second range 624 may be identical and/or overlap with first range 612 and/or may be combined with first range via Cartesian product or the like to generate a mapping permitting evaluation overlap of first fuzzy set 604 and second fuzzy set 616. Where first fuzzy set 604 and second fuzzy set 616 have a region 636 that overlaps, first membership function 608 and second membership function 620 may intersect at a point 632 representing a probability, as defined on probability interval, of a match between first fuzzy set 604 and second fuzzy set 616. Alternatively or additionally, a single value of first and/or second fuzzy set may be located at a locus 636 on first range 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a non-limiting example, represent a degree of match between first fuzzy set 604 and second fuzzy set 616, and/or single values therein with each other or with either set, which is sufficient for purposes of the matching process; for instance, the classification into one or more query categories may indicate a sufficient degree of overlap with fuzzy set representing contextual data 108 and query response data for combination to occur as described above. Each threshold may be established by one or more user inputs. Alternatively or additionally, each threshold may be tuned by a machine-learning and/or statistical process, for instance and without limitation as described in further detail below.

In an embodiment, a degree of match between fuzzy sets may be used to rank one resource against another. For instance, if both contextual data 108 and query response data have fuzzy sets, query response data may be generated by having a degree of overlap exceeding a predictive threshold, processor 104 may further rank the two resources by ranking a resource having a higher degree of match more highly than a resource having a lower degree of match. Where multiple fuzzy matches are performed, degrees of match for each respective fuzzy set may be computed and aggregated through, for instance, addition, averaging, or the like, to determine an overall degree of match, which may be used to rank resources; selection between two or more matching resources may be performed by selection of a highest-ranking resource, and/or multiple notifications may be presented to a user in order of ranking.

Figure 7:
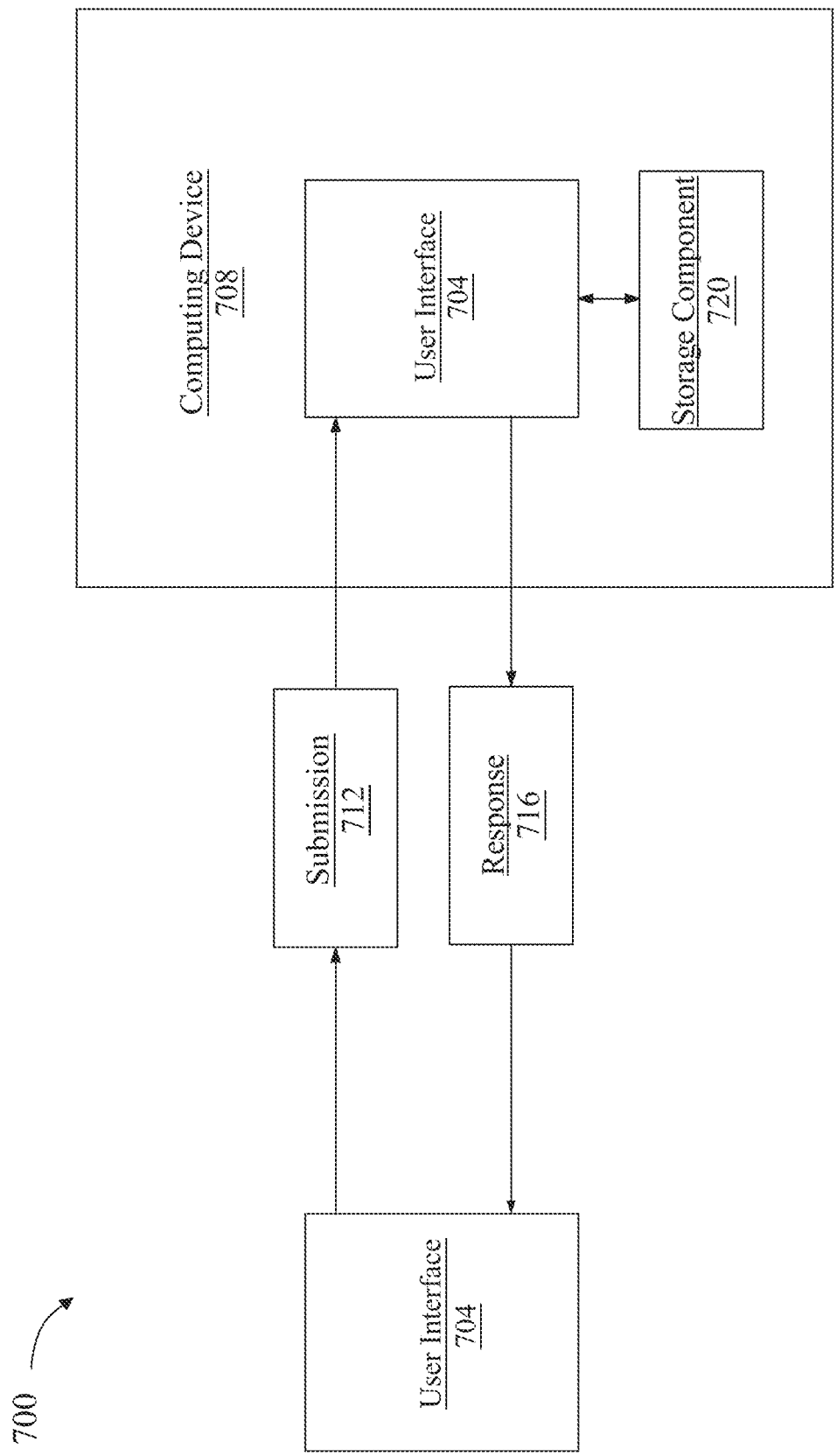
FIG. 7 is an illustration of an exemplary embodiment of a chatbot.

Referring to FIG. 7, a chatbot system 700 is schematically illustrated. According to some embodiments, a user interface 704 may be communicative with a computing device 708 that is configured to operate a chatbot. In some cases, user interface 704 may be local to computing device 708. Alternatively or additionally, in some cases, user interface 704 may remote to computing device 708 and communicative with the computing device 708, by way of one or more networks, such as without limitation the internet. Alternatively or additionally, user interface 704 may communicate with user device 708 using telephonic devices and networks, such as without limitation fax machines, short message service (SMS), or multimedia message service (MMS). Commonly, user interface 704 communicates with computing device 708 using text-based communication, for example without limitation using a character encoding protocol, such as American Standard for Information Interchange (ASCII). Typically, a user interface 704 conversationally interfaces a chatbot, by way of at least a submission 712, from the user interface 708 to the chatbot, and a response 716, from the chatbot to the user interface 704. In many cases, one or both of submission 712 and response 716 are text-based communication. Alternatively or additionally, in some cases, one or both of submission 712 and response 716 are audio-based communication.

Continuing in reference to FIG. 7, a submission 712 once received by computing device 708 operating a chatbot, may be processed by a processor. In some embodiments, processor processes a submission 712 using one or more of keyword recognition, pattern matching, and natural language processing. In some embodiments, processor employs real-time learning with evolutionary algorithms. In some cases, processor may retrieve a pre-prepared response from at least a storage component 720, based upon submission 712. Alternatively or additionally, in some embodiments, processor communicates a response 716 without first receiving a submission 712, thereby initiating conversation. In some cases, processor communicates an query to user interface 704; and the processor is configured to process an answer to the query in a following submission 712 from the user interface 704. In some cases, an answer to a query present within submission 712 from a user device 704 may be used by computing device 708 as an input to another function.

With continued reference to FIG. 7, A chatbot may be configured to provide a user with a plurality of options as an input into the chatbot. Chatbot entries may include multiple choice, short answer response, true or false responses, and the like. A user may decide on what type of chatbot entries are appropriate. In some embodiments, the chatbot may be configured to allow the user to input a freeform response into the chatbot. The chatbot may then use a decision tree, data base, or other data structure to respond to the users entry into the chatbot as a function of a chatbot input. As used in the current disclosure, "Chatbot input" is any response that a candidate or employer inputs into a chatbot as a response to a prompt or question.

With continuing reference to FIG. 7, computing device 708 may be configured to respond to a chatbot input using a decision tree. A "decision tree," as used in this disclosure, is a data structure that represents and combines one or more determinations or other computations based on and/or concerning data provided thereto, as well as earlier such determinations or calculations, as nodes of a tree data structure where inputs of some nodes are connected to outputs of others. Decision tree may have at least a root node, or node that receives data input to the decision tree, corresponding to at least a candidate input into a chatbot. Decision tree has at least a terminal node, which may alternatively or additionally be referred to herein as a "leaf node," corresponding to at least an exit indication; in other words, decision and/or determinations produced by decision tree may be output at the at least a terminal node. Decision tree may include one or more internal nodes, defined as nodes connecting outputs of root nodes to inputs of terminal nodes. Computing device 708 may generate two or more decision trees, which may overlap; for instance, a root node of one tree may connect to and/or receive output from one or more terminal nodes of another tree, intermediate nodes of one tree may be shared with another tree, or the like.

Still referring to FIG. 7, computing device 708 may build decision tree by following relational identification; for example, relational indication may specify that a first rule module receives an input from at least a second rule module and generates an output to at least a third rule module, and so forth, which may indicate to computing device 708 an in which such rule modules will be placed in decision tree. Building decision tree may include recursively performing mapping of execution results output by one tree and/or subtree to root nodes of another tree and/or subtree, for instance by using such execution results as execution parameters of a subtree. In this manner, computing device 708 may generate connections and/or combinations of one or more trees to one another to define overlaps and/or combinations into larger trees and/or combinations thereof. Such connections and/or combinations may be displayed by visual interface to user, for instance in first view, to enable viewing, editing, selection, and/or deletion by user; connections and/or combinations generated thereby may be highlighted, for instance using a different color, a label, and/or other form of emphasis aiding in identification by a user. In some embodiments, subtrees, previously constructed trees, and/or entire data structures may be represented and/or converted to rule modules, with graphical models representing them, and which may then be used in further iterations or steps of generation of decision tree and/or data structure. Alternatively or additionally subtrees, previously constructed trees, and/or entire data structures may be converted to APIs to interface with further iterations or steps of methods as described in this disclosure. As a further example, such subtrees, previously constructed trees, and/or entire data structures may become remote resources to which further iterations or steps of data structures and/or decision trees may transmit data and from which further iterations or steps of generation of data structure receive data, for instance as part of a decision in a given decision tree node.

Continuing to refer to FIG. 7, decision tree may incorporate one or more manually entered or otherwise provided decision criteria. Decision tree may incorporate one or more decision criteria using an application programmer interface (API). Decision tree may establish a link to a remote decision module, device, system, or the like. Decision tree may perform one or more database lookups and/or look-up table lookups. Decision tree may include at least a decision calculation module, which may be imported via an API, by incorporation of a program module in source code, executable, or other form, and/or linked to a given node by establishing a communication interface with one or more exterior processes, programs, systems, remote devices, or the like; for instance, where a user operating system has a previously existent calculation and/or decision engine configured to make a decision corresponding to a given node, for instance and without limitation using one or more elements of domain knowledge, by receiving an input and producing an output representing a decision, a node may be configured to provide data to the input and receive the output representing the decision, based upon which the node may perform its decision.

Figure 8:
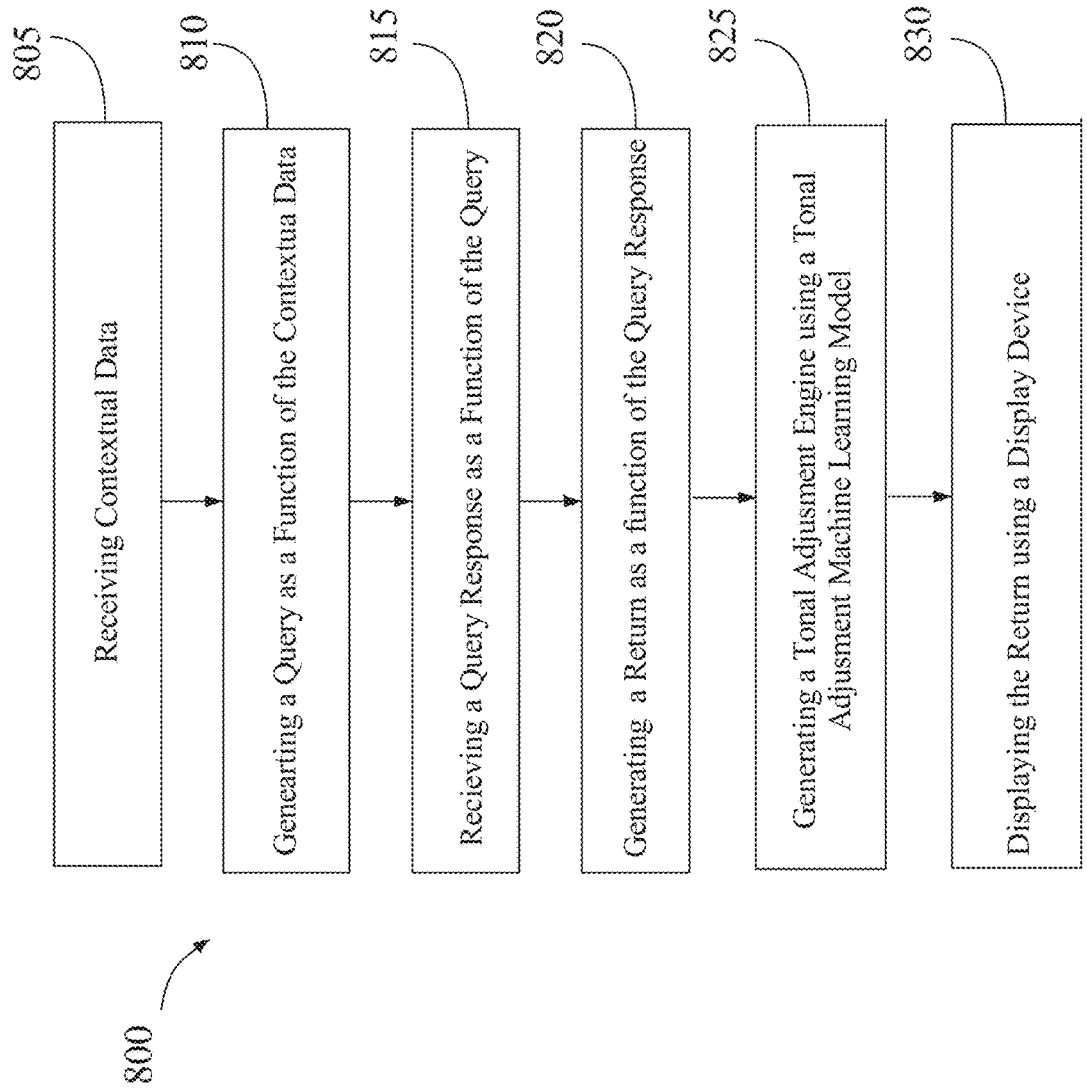
FIG. 8 is a flow diagram of an exemplary method for generating a text report.

Referring now to FIG. 8, a flow diagram of an exemplary method 800 for generating a text report is illustrated. At step 805, method 800 includes receiving, using at least a processor, contextual data. This may be implemented as described and with reference to FIGS. 1-7. In an embodiment, the contextual data may include at least a datum associated with a user's medical history.

Still referring to FIG. 8, at step 810, method 800 includes generating, using the at least a processor, a query as a function of the contextual data. This may be implemented as described and with reference to FIGS. 1-7. In an embodiment, wherein the query machine learning model includes a large language model. IN another embodiment, the first set of queries may be presented to the user using a chatbot.

Still referring to FIG. 8, at step 815, method 800 includes receiving, using the at least a processor, a query responses as a function of the query. This may be implemented as described and with reference to FIGS. 1-7. In an embodiment, receiving a query response comprises an query machine learning model.

Still referring to FIG. 8, at step 820, method 800 includes generating, using the at least a processor, a return as a function of the query response. This may be implemented as described and with reference to FIGS. 1-7.

Still referring to FIG. 8, at step 825, method 800 includes generating a tonal adjustment engine using a tonal adjustment machine learning model. This may be implemented as described and with reference to FIGS. 1-7. In an embodiment, the method may include training a tonal adjustment machine learning model using tonal adjustment training data. The tonal adjustment machine engine may alter at least a tone of the response as a function of the contextual data. The method may generate a response as a function of a level of user knowledge and the user's education model. The tonal adjustment machine learning model may include a large language machine learning model.

Still referring to FIG. 8, at step 830, method 800 includes displaying, using the at least a processor, the response using a display device.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
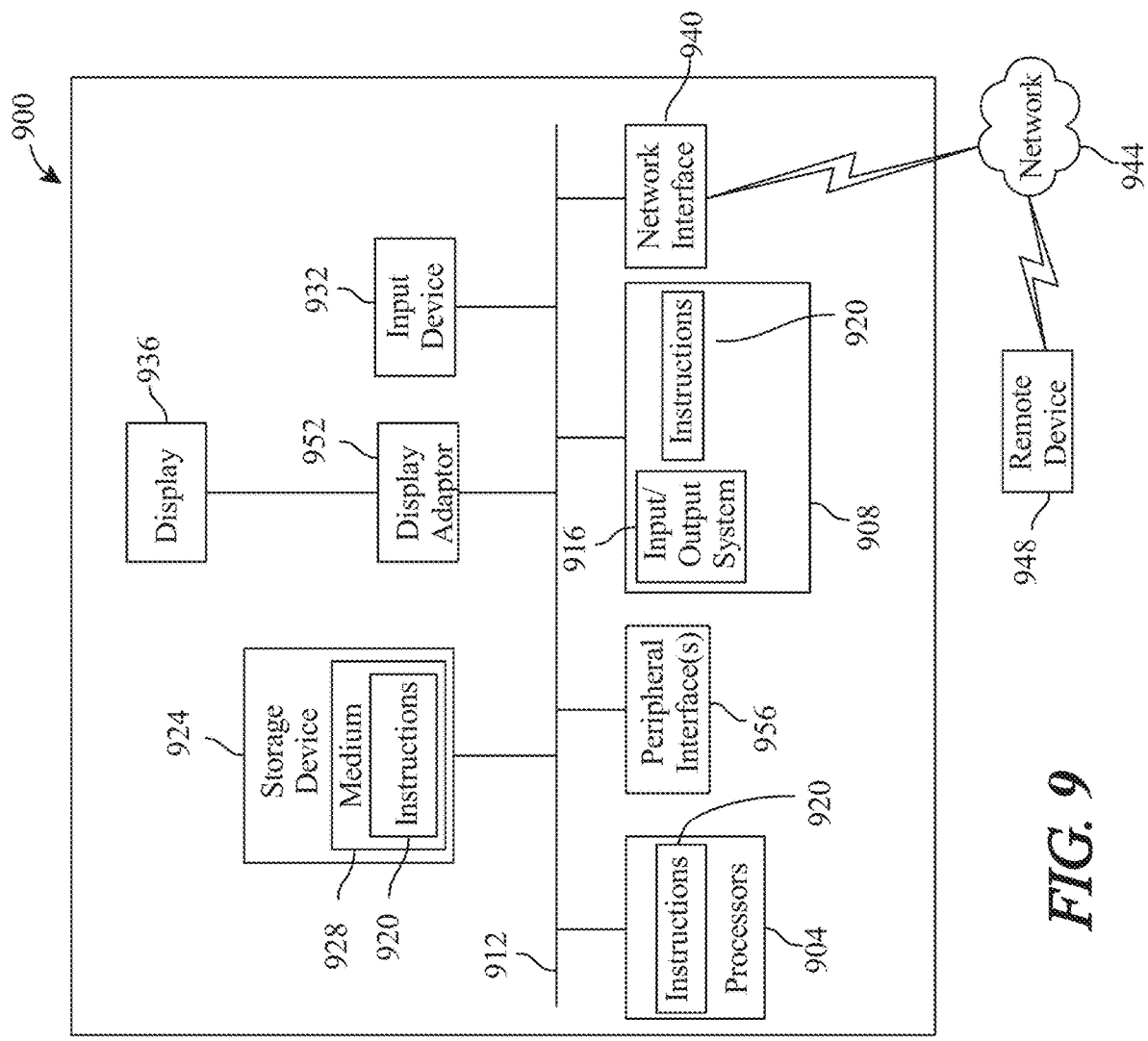
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. An apparatus for generating a text output, the apparatus comprising:
   at least a processor; and
   a memory communicatively connected to the at least a processor, wherein the memory contains instructions configuring the at least a processor to:
   receive contextual data;
   generate a query as a function of the contextual data;
   receive a query response as a function of the query;
   generate a return as a function of the query response;
   generate a tonal adjustment engine, wherein generating the tonal adjustment engine comprises:
      creating a tonal adjustment training data, wherein the tonal adjustment training data comprises the contextual data as inputs correlated to examples of the query as outputs;
      training iteratively a tonal adjustment machine learning model using the tonal adjustment training data; and
      updating the tonal adjustment engine as a function of the outputs; and
   display the return using a display device.

2. The apparatus of claim 1, wherein the contextual data comprises at least datum associated with a user's medical history.

3. The apparatus of claim 1, wherein generating the query response comprises using a query machine learning model.

4. The apparatus of claim 1, wherein the tonal adjustment engine alters at least a tone of the response as a function of the contextual data.

5. The apparatus of claim 1, wherein the tonal adjustment engine comprises instructions for rephrasing the response as a function of the contextual data.

6. The apparatus of claim 1, wherein the return is a function of a level of a user's knowledge.

7. The apparatus of claim 6, wherein the level of the user's knowledge is a function of at least an education level of the user.

8. The apparatus of claim 1, wherein the tonal adjustment machine learning model is a large language machine learning model.

9. The apparatus of claim 8, wherein the tonal adjustment machine learning model comprises at least a general training set wherein the at least a general training set comprises a variety of data sets.

10. The apparatus of claim 9, wherein the tonal adjustment machine learning model comprises at least a specific training set wherein the at least a specific training set comprises data including specific correlations.

11. A method for generating a medical report, the method comprising:
    receiving, using at least a processor, contextual data;
    generating, using the at least a processor, a query as a function of the contextual data;
    receiving, using the at least a processor, a query response as a function of the query;
    generating, using the at least a processor, a return as a function of the query response;
    generate a tonal adjustment engine, wherein generating the tonal adjustment engine comprises:
       creating a tonal adjustment training data, wherein the tonal adjustment training data comprises the contextual data as inputs correlated to examples of the query as outputs;
       training iteratively a tonal adjustment machine learning model using the tonal adjustment training data; and
       updating the tonal adjustment engine as a function of the outputs; and
    displaying the return using a display device.

12. The method of claim 11, wherein the contextual data comprises at least datum associated with a user's medical history.

13. The method of claim 11, wherein generating the query response comprises using a query machine learning model.

14. The method of claim 11, wherein the tonal adjustment engine alters at least a tone of the response as a function of the contextual data.

15. The method of claim 11, wherein the tonal adjustment engine comprises instructions for rephrasing the response as a function of the contextual data.

16. The method of claim 11, wherein the return is a function of a level of a user's knowledge.

17. The method of claim 16, wherein the level of the user's knowledge is a function of at least an education level of the user.

18. The method of claim 11, wherein the tonal adjustment machine learning model is a large language machine learning model.

19. The method of claim 18, wherein the tonal adjustment machine learning model comprises at least a general training set wherein the at least a general training set comprises a variety of data sets.

20. The method of claim 19, wherein the tonal adjustment machine learning model comprises at least a specific training set wherein the at least a specific training set comprises data including specific correlations.

\* \* \* \* \*